US008962885B2

(12) United States Patent
Grenda et al.

(10) Patent No.: US 8,962,885 B2
(45) Date of Patent: Feb. 24, 2015

(54) β-HYDROXYALKYLAMIDES, A METHOD FOR PRODUCTION OF SAME AND USE OF SAME

(75) Inventors: Werner Grenda, Herne (DE); Emmanouil Spyrou, Schermbeck (DE); Thomas Weihrauch, Duelmen (DE); Christoph Lammers, Recklinghausen (DE); Holger Loesch, Herne (DE); Klaus Behrendt, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/045,129

(22) Filed: Mar. 10, 2011

(65) Prior Publication Data
US 2012/0208956 A1 Aug. 16, 2012

(30) Foreign Application Priority Data

Mar. 11, 2010 (DE) .......................... 10 2010 002 783
Mar. 10, 2011 (DE) .......................... 10 2011 005 332

(51) Int. Cl.
| | | |
|---|---|---|
| C07C 231/02 | (2006.01) | |
| C07C 1/32 | (2006.01) | |
| C07C 235/44 | (2006.01) | |
| C07C 233/64 | (2006.01) | |
| C07C 233/60 | (2006.01) | |

(52) U.S. Cl.
CPC ............ *C07C 231/02* (2013.01); *C07C 1/323* (2013.01); *C07C 235/44* (2013.01); *C07C 233/64* (2013.01); *C07C 233/60* (2013.01)

USPC ........................... 564/134; 564/138; 564/152

(58) Field of Classification Search
CPC .... C07C 1/323; C07C 231/02; C07C 233/64; C07C 235/44
USPC ......................................... 564/134, 138, 152
See application file for complete search history.

(56) References Cited

U.S. PATENT DOCUMENTS 6,194,613 B1 2/2001 Weihrauch et al.
2011/0039981 A1 2/2011 Hefner et al.

FOREIGN PATENT DOCUMENTS

| JP | 49-26226 | 3/1974 |
|---|---|---|
| KR | 10-2009-0111720 | * 10/2009 |
| WO | WO 2009-143037 | * 11/2009 |
| WO | WO 2009/143037 A1 | 11/2009 |

OTHER PUBLICATIONS

Jung, Journal of the Korean Industrial and Engineering Chemistry, vol. 20, No. 2, Apr. 2009, p. 195-200.*
Machine translation of KR 10-2009-0111720, Oct. 2009.*
International Search Report issued Jun. 9, 2011, in Patent Application No. PCT/EP2011/053606 (with English Translation of Category of Cited Documents).

(Continued)

*Primary Examiner* — Robert C Boyle
(74) *Attorney, Agent, or Firm* — Oblon, Spivak, McClelland, Maier & Neustadt, L.L.P.

(57) ABSTRACT

The invention relates to new β-hydroxyalkylamides, to a method for production of same and to the use of same.

32 Claims, 14 Drawing Sheets

DSC diagram of the β-hydroxyalkylamide of Formula XIIA described in Example 3b

(56) References Cited

OTHER PUBLICATIONS

Hong-Ryun Jung, et al., "Preparation and Properties of $N^1$,$N^1$,$N^4$,$N^4$-Tetrakis(hydroxyethyl)cyclohexane-*trans*-1,4-dicarboxamide as a Crosslinker of Polyester Powder Coatings", Journal of the Korean Industrial and Engineering Chemistry, vol. 20, No. 2, XP 9148131, Apr. 2009, pp. 195-200 (with English Abstract).

Jung,H-R, et al., Preparation and Properties of $N^1$, $N^1$, $N^4$, $N^4$-Tetrakis(hydroxyethyl)cyclohexane-trans-1,4-dicarboxamide as A Crosslinker of Polyester Powder Coatings, *J. Korean Ind. Eng. Chem.*, vol. 20, No. 2, Apr. 2009, p. 195.

* cited by examiner

Fig.2 13CNMR_DEPT135 DMSO+Cr(acac)3

Fig. 5 DSC diagram of the β-hydroxyalkylamide of Formula XIIA described in Example 3a Fig. 6 DSC diagram of the β-hydroxyalkylamide of Formula XIIA described in Example 3b Fig. 8  DSC diagram of the β-hydroxyalkylamide described in Example 4c Fig. 9 XRPD (x-ray powder diffraction) analysis of the β-hydroxyalkylamide of Formula XIIA (matting material) described in Example 3a Fig. 10 XRPD (x-ray powder diffraction) analysis of the β-hydroxyalkylamide (non-matting material) described in Example 4c Fig. 11 XRPD (x-ray powder diffraction) analysis of the β-hydroxyalkylamide of Formula XIIA (matting material) described in Example 4b

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

*Fig. 12*

Table 5: Characteristic XRPD peaks (in degrees 2 theta) of the β-hydroxyalkylamide of Formula XIIA (matting material) described described in Example 3a

| Peak No. | Degrees 2 theta ± 0.2 degrees 2 theta | d (Å) |
|---|---|---|
| 1 | 8.90 | 9.93 |
| 2 | 13.90 | 6.37 |
| 3 | 17.10 | 5.18 |
| 4 | 17.60 | 5.04 |
| 5 | 18.50 | 4.79 |
| 6 | 19.00 | 4.67 |
| 7 | 22.20 | 4.00 |
| 8 | 23.40 | 3.80 |
| 9 | 24.00 | 3.71 |
| 10 | 24.60 | 3.62 |
| 11 | 25.40 | 3.50 |
| 12 | 28.70 | 3.11 |
| 13 | 32.00 | 2.80 |
| 14 | 37.30 | 2.41 |

*Fig. 13*

Table 6: Characteristic XRPD peaks (in degrees 2 theta) of the β-hydroxyalkylamide (non-matting material) described in Example 4c

β-HYDROXYALKYLAMIDES, A METHOD FOR PRODUCTION OF SAME AND USE OF SAME

The invention relates to new β-hydroxyalkylamides, to a method for production of same and to the use of same.

β-Hydroxyalkylamides are valuable intermediate products in organic syntheses.

For ten years, β-hydroxyalkylamides have found technical applications as curing agents (also known as cross-linking agents) in powder lacquers.

β-Hydroxyalkylamides as well as methods for production of same are known from the following patent documents: DE 2509237, DE19823925, EP 0473380, EP 0960878, WO 2000050384, WO 200055266.

Powder lacquers based on triglycidyl isocyanurate (TGIC) as cross-linking agent (curing agent) and acid-functional polyesters yield corrosion-resistant and weatherproof powder coatings. However, TGIC is classified as mutagenic and toxic.

β-Hydroxyalkylamides are toxicologically safe and also more reactive as cross-linking agents. In U.S. Pat. Nos. 4,076,917 and 4,101,606, powder lacquers are obtained by combining β-hydroxyalkylamides with polymers containing at least one carboxylate or anhydride function, especially with polyacrylates. EP 0322834 describes thermally curing powder lacquers composed of polyesters containing acid groups and of β-hydroxyalkylamides.

Coating systems imparting a uniformly level and matte surface to a substrate command particular interest. The reason is of predominantly practical nature. Glossy surfaces require much more intensive cleaning than do matte surfaces. Furthermore, safety considerations may make it desirable to avoid highly reflective surfaces. Broad sectors of the powder-lacquer industry, such as the architecture, automobile and metal-furniture sectors, are seeing a rising demand for matte (10-30 units) and semi-matte (30-50 units) surfaces, measured as reflectometer values according to DIN 67530/ISO 2813 at an angle of incidence of 60°.

The simplest principle by which a matte surface can be obtained is to admix fillers such as chalk, finely divided silicon dioxide or barium sulfate with the powder lacquer in lower or higher proportions, depending on the desired matte effect. However, such additives lead to deterioration of the lacquer-specific properties, such as adhesion, flexibility, impact resistance and chemical resistance.

The addition of substances incompatible with the lacquer, such as waxes or cellulose derivatives, indeed achieves distinct matting. However, slight changes during extrusion lead to fluctuations in surface gloss and to fade-out in dark color tones. Reproducibility of the matte effect is not guaranteed.

EP 0698645 describes the creation of matte powder coatings by means of dry mixing (dry blend) of at least two separately manufactured hydroxyalkylamide powder lacquers.

For semi-matte and matte (<50 gloss units) powder coatings containing hydroxyalkyamides, therefore, dry blends represent the state of the art. In other words, two hydroxyalkylamide powder lacquers having different acid numbers in the binder components must be separately produced then added as a dry mixture to the grinding process. This imposes considerable extra time and effort and, if any binder component suffers from deviations, leads to gloss deviations, which require considerable additional time and effort to correct. Furthermore, these dry mixtures separate even in the possession of the end customer, with a resulting shift in gloss, if the powder lacquer is scheduled to be recycled in the usual way.

Korean Unexamined Application KR 10-2009-0111720 (Application Number 10-2008-0037454), whose title is translated as "CYCLOALKANE DICARBOXAMIDE COMPOUNDS, THEIR PREPARATION AND APPLICATION" (see also J. Korean Ind. Eng. Chem., Vol. 20, No. 2, April 2009, 195-200), discloses in Example 1 in particular the compound referred to therein as $N^1,N^1,N^4,N^4$-tetrakis(2-hydroxyethyl)cyclohexane-1,4-dicarboxamide (Formula 3). According to FIG. 2, this compound has only one peak in the DSC analysis, with a maximum peak at approximately 190° C. A cis/trans content of the compound is not mentioned. Furthermore, a comparison is made between carboxyl-group-containing polyesters—which are not precisely defined but are indicated only by broad ranges of some parameters (polyesters not unambiguously characterized and unknown with this viscosity on the market)—which are cross-linked either with this compound or with the known β-hydroxyalkylamides, referred to therein in Example 3 as $[N^1,N^1,N^6,N^6$-tetrakis(2-hydroxyethyl)adipamide] (obtainable as VESTAGON HAA 320 or PRIMID XL 552), or in other words with prior art curing agents that are long-established commercial products and that, as known, lead to glossy surfaces of the manufactured coatings. The sheets are illustrated in FIGS. 3 and 4. The description does not indicate that matte coatings are involved. This would not even be possible, since glossy coatings are obtained with the conventional curing agents.

The object of the present invention was to find new β-hydroxyalkylamides that can be used as intermediate products and curing agents. In particular, the object of the invention was to find new β-hydroxyalkylamides that lead to matte surfaces in powder lacquers after curing and that do not require any dry mixture for production of the powder lacquers.

BRIEF DESCRIPTION OF THE DRAWINGS

FIG. 5 shows a DSC diagram of the β-hydroxyalkylamide of Formula XIIA described in Example 3a.

FIG. 9 shows a XRPD (x-ray powder diffraction) analysis of the β-hydroxyalkylamide of Formula XIIA (matting material) described in Example 3a.

FIG. 12 shows a Characteristic XRPD peaks (in degrees 2 theta) of the β-hydroxyalkylamide of Formula XIIA (matting material) described in Example 3a.

FIG. 13 shows a Characteristic XRPD peaks (in degrees 2 theta) of the β-hydroxyalkylamide (non-matting material) described in Example 4c.

Figure 1:
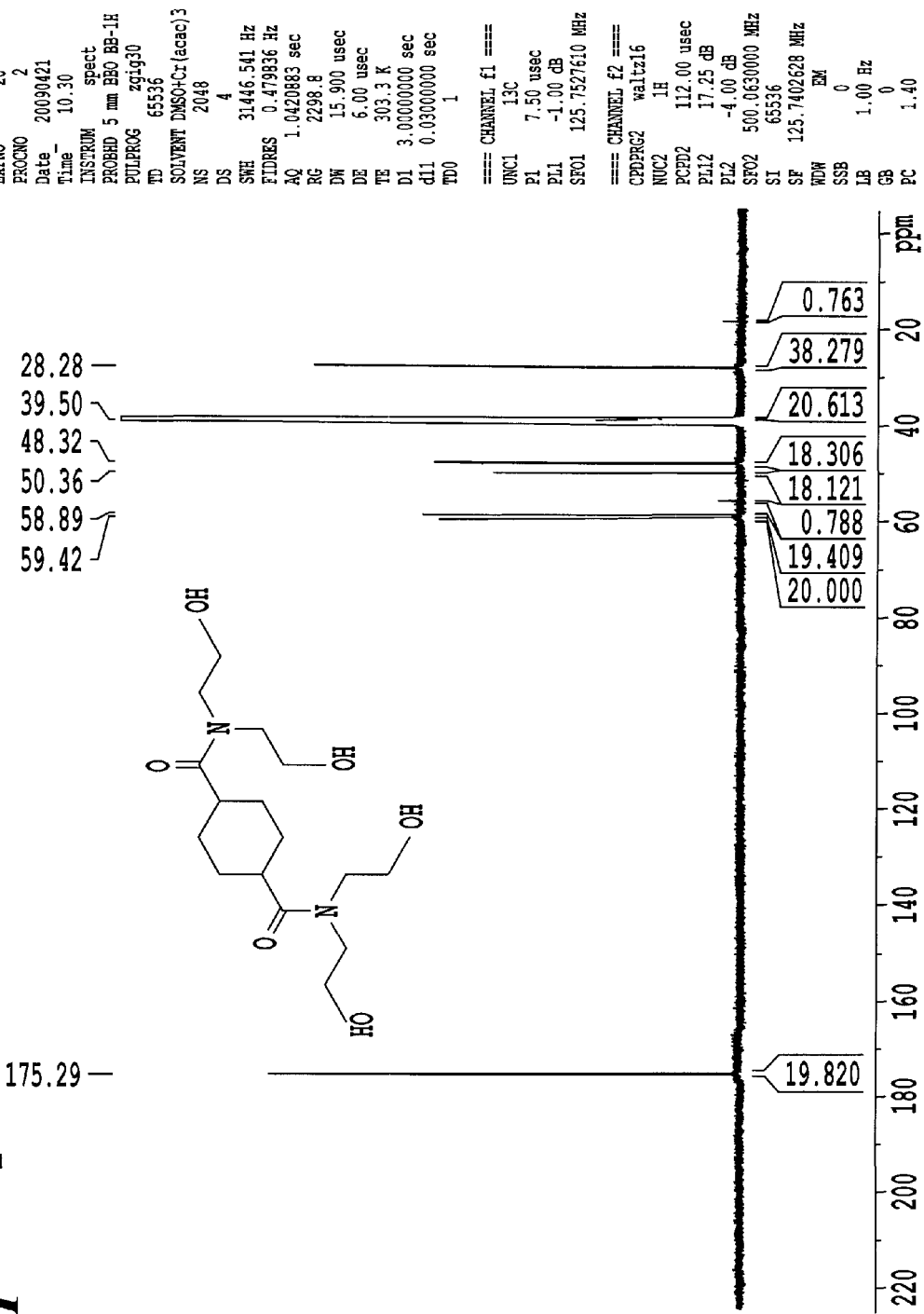
FIGS. 1-4 show NMR spectra of trans-N,N,N',N'-tetrakis-(2-hydroxyethyl)cyclohexyl-1,4-diamide (formula XII).

The object was achieved by the inventive new β-hydroxyalkylamides.

Subject matter of the invention are β-hydroxyalkylamides having two or three or four β-hydroxyalkylamide groups per molecule of formula I

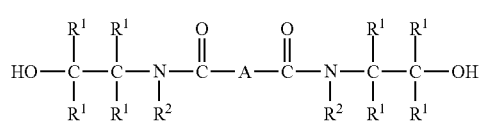

where
R$^1$, R$^2$: independently of one another denote the same or different radicals, selected from alkyl radicals, cycloalkyl radicals, aryl radicals, aralkyl radicals or alkenyl radicals having 1-24 carbon atoms, wherein the radicals may also contain heteroatoms and/or functional groups and wherein R$^1$ may also be hydrogen,
and wherein R$^2$ may also be

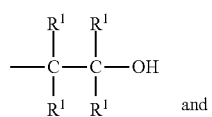

A:

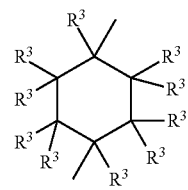

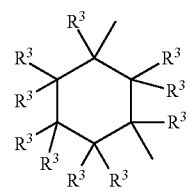

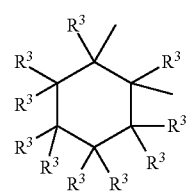

where R$^3$: independently of one another denote the same or different radicals, selected from hydrogen, alkyl radicals, cycloalkyl radicals, aryl radicals, aralkyl radicals or alkenyl radicals having 1-24 carbon atoms, wherein the radicals may also contain heteroatoms and/or functional groups and wherein two or more R$^3$ substituents may be linked to one another to form rings;
wherein the β-hydroxyalkylamides exist in solid form below 150° C.

Surprisingly, it has been found that β-hydroxyalkylamides having a cyclohexane ring in the skeleton, with the proviso that the β-hydroxyalkylamides exist in solid form below 150° C., lead to matte surfaces after curing in powder lacquers. Moreover, the inventive β-hydroxyalkylamides represent new intermediate products.

The β-hydroxyalkylamides can be produced from various starting materials. A known method is the reaction of β-hydroxyalkylamines with esters of carboxylic acids, the latter generating the basic skeleton (A). Depending on the choice of starting materials, the inventive β-hydroxyalkylamides can be produced in this way.

Alternative but less preferred methods are based on other carboxylic acid derivatives, such as carboxylic acids, carboxylic acid chlorides, carboxylic acid anhydrides or other activated carboxylic acid derivatives as starting materials, which are reacted with β-hydroxyalkylamines.

Suitable β-hydroxyalkylamines are such containing alkyl groups having at least 2 to 10 carbon atoms in the hydrocarbon skeleton. The alkyl groups may be linear, branched or even cyclic. Likewise, the alkyl groups may be substituted with hetero atoms, preferably oxygen and nitrogen. Furthermore, these alkyl groups may also contain functional groups, preferably carbonyl groups, carboxyl groups, amino groups, amide groups and urethane groups, and may have an additional alkyl radical on the nitrogen.

In this invention the β-hydroxyalkylamides are preferably produced from N-alkyl-1,2-alkanolamines and/or from N,N-bis-2-hydroxyalkylamines and esters of cyclohexanedicarboxylic acids.

Particularly preferably, there are used β-hydroxyalkylamines of formulas II and/or III:

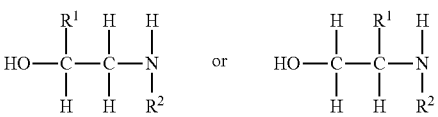

Formulas II where
R$^1$ denotes hydrogen, methyl, ethyl, propyl,
R$^2$ denotes methyl;

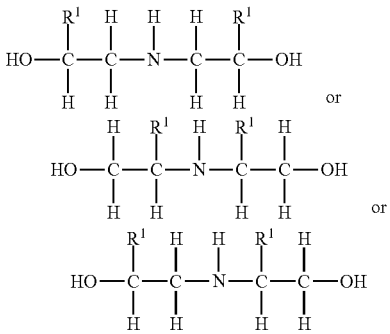

Formulas III where R$^1$ denotes hydrogen, methyl, ethyl, propyl, either simultaneously or independently of one another.

According to the invention, the following compounds are used particularly preferably as starting materials for production of the β-hydroxyalkylamides: diethanolamine (DEA), diisopropanolamine (DIPA), di-sec-butanolamine, N-methylethanolamine, N-methyl-isopropanolamine.

1,2-Substituted, 1,3-substituted and 1,4-substituted cyclohexanedicarboxylic acid derivatives, especially cyclohexanedicarboxylic acid dialkyl esters, are suitable as starting compounds for substituents A in the inventive β-hydroxyalkylamides. These starting compounds may have any desired cis/trans content.

Preferably there are used compounds of formula IV:

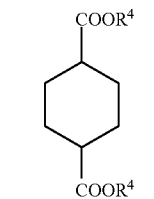
$A^4$

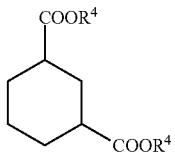
$A^5$

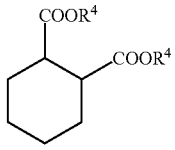
$A^6$ where $R^4$ denotes methyl, ethyl, propyl, butyl simultaneously or independently of one another.

Particularly preferably there are used 1,4-substituted cyclohexanedicarboxylic acid esters, most particularly preferably dimethyl-1,4-cyclohexyl dicarboxylate.

Those β-hydroxyalkylamides of dialkyl-1,4-cyclohexyldicarboxylates, preferably of dimethyl-1,4-cyclohexyldicarboxylate, which are particularly preferred according to the invention have a trans content, relative to the position of the carboxyl groups on the cyclohexyl ring, of greater than or equal to 70 mol %, preferably greater than 80 mol % and particularly preferably greater than 85 mol %. In this connection, dialkyl-1,4-cyclohexyldicarboxylates having any desired trans content may be used.

The inventive β-hydroxyalkylamides (I) exist in solid form below 150° C., preferably below 170° C., particularly preferably below 180° C.

As secondary products, the β-hydroxyalkylamides also contain small amounts of dimers, trimers, oligomers and other condensation products of the target product.

Particularly preferred inventive β-hydroxyalkylamides have the following formulas:

Formula V
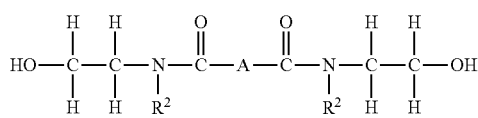

Formula VI
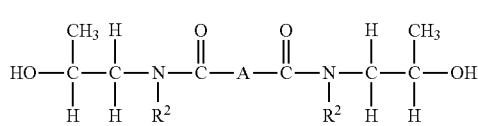

Formula VII
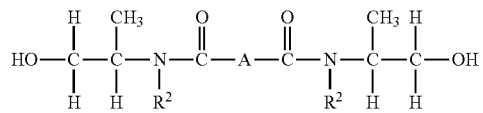

Formula VIII
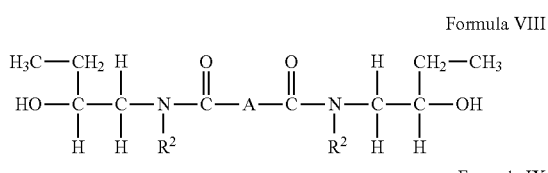

Formula IX
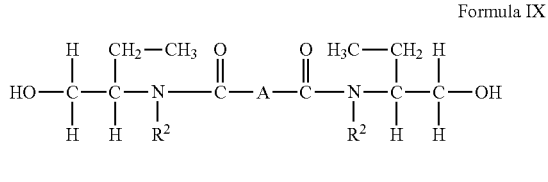

Formula X
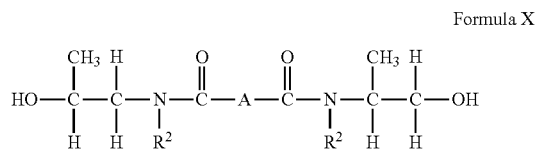

Formula XI
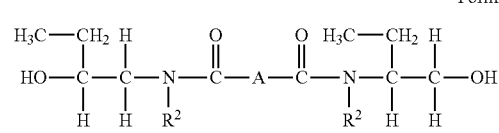

where
$R^2$: methyl, or

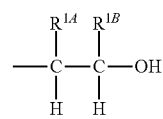

where $R^{1A}$ denotes hydrogen and $R^{1B}$ denotes methyl, ethyl, propyl, or where $R^{1A}$ denotes methyl, ethyl, propyl and $R^{1B}$ denotes hydrogen; and A: 1,4-disubstituted cyclohexane ring of the formula

wherein the trans content of A is ≥70 mol %;

and wherein the β-hydroxyalkylamides exist in solid form below 150° C.

That β-hydroxyalkylamide of dimethyl-1,4-cyclohexyldicarboxylate and diethanolamine which is particularly preferred according to the invention and has four β-hydroxyalkylamide groups per molecule according to formula XII Formula XII

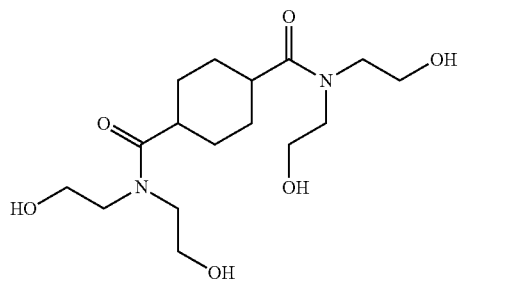

has a trans content on the cyclohexyl ring of greater than or equal to 70 mol %, preferably greater than 80 mol % and particularly preferably greater than 85 mol %.

In principle, the inventive β-hydroxyalkylamides may be produced by known methods, for example according to DE 2509237, DE19823925, EP 473380, EP 960878, WO 2000050384, WO 200055266. The method may be carried out continuously, semicontinuously or discontinuously, as in the batch method, for example.

Preferably, however, the continuous method described in detail hereinafter will be used for production of the β-hydroxyalkylamides from dialkyl-1,4-cyclohexyl dicarboxylates.

The invention also relates to a method for solvent-free, continuous production of the preferred inventive β-hydroxyalkylamides from dialkyl-1,4-cyclohexyl dicarboxylates, especially from dimethyl-1,4-cyclohexyl dicarboxylate, having a trans content on the cyclohexyl ring of greater than or equal to 70 mol %, preferably greater than 80 mol % and particularly preferably greater than 85 mol %, and existing in solid form below 150° C., in an extruder, intensive kneader, intensive mixer or static mixer.

Surprisingly, it has been found that enrichment of the trans form to 70 mol % trans or more on the 1,4-disubstituted cyclohexane ring takes place very easily during production of the β-hydroxyalkylamides by means of a continuous method in an extruder, intensive kneader, intensive mixer or static mixer. For this purpose it is possible to use dialkyl-1,4-cyclohexyl dicarboxylates that have any desired trans content.

In the dialkyl-1,4-cyclohexyl dicarboxylate starting product used according to the invention, the trans configuration is usually between 15 and 35 mol %, depending on raw-material source. However, any desired isomeric composition may be used.

Subject matter of the invention is therefore a method for solvent-free and continuous production of β-hydroxyalkylamides having at least two or three or four β-hydroxyalkylamide groups per molecule of formula I Formula I

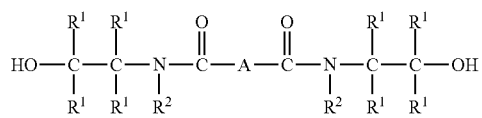

where
R¹, R²: independently of one another denote the same or different radicals, selected from alkyl radicals, cycloalkyl radicals, aryl radicals, aralkyl radicals or alkenyl radicals having 1-24 carbon atoms, wherein the radicals may also contain heteroatoms and/or functional groups and wherein R¹ may also be hydrogen
and wherein R² may also be

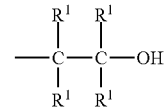

and
A: 1,4-disubstituted cyclohexane ring of the formula

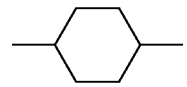

wherein the trans content of A is ≥70 mol %; and
wherein the β-hydroxyalkylamides (I) exist in solid form below 150° C., in an extruder, intensive kneader, intensive mixer or static mixer.

The principle of the method is that the conversion of the feed substances takes place continuously in an extruder, intensive kneader, intensive mixer or static mixer by intensive intermixing and short-time reaction, preferably with heat input.

Temperatures of 50 to 325° C. may be used in the method, the temperatures varying according to the product, as shown in the examples.

Intensive intermixing and short-time reaction with heat input means that the dwell time of the feed substances in the aforesaid machines usually ranges from 3 seconds to 15 minutes, preferably 3 seconds to 5 minutes, particularly preferably 5 to 180 seconds. In the process, the reactants are made to react within a short time with heat input at temperatures of 50° C. to 325° C., preferably 50 to 225° C., most particularly preferably 70 to 200° C. Depending on the nature of the feed substances and of the end products, however, these values of dwell time and temperature may also fall within other preferred ranges.

If necessary, the process is followed by a continuous after-reaction. Completeness of the reaction is ensured by removal of the alcohols formed during amidation. This removal is preferably achieved by evacuating the alcohols by means of vacuum via apertures in the housings of the extruder or intensive kneader or intensive mixer or static mixer and/or by passing a gas stream over the intensively mixed reaction mixture, thus entraining the more volatile alcohols in the gas stream.

The reaction may be accelerated by catalysts. Suitable catalysts are hydroxides and/or alcoholates of alkali metals, such as sodium or potassium hydroxide, sodium or potassium methanolate, quaternary ammonium hydroxides, alkoxides and/or other strong bases. The concentration is 0.01 to 5%, preferably 0.1 to 3% relative to the total mass used.

The arrangement of vacuum domes or gas-passage stations may be variable, and will depend on the nature of the starting materials and of the resulting alcohols. A station for removal of residual amounts of alcohol may also be added downstream from the actual reaction part.

The end product can then be obtained by subsequent rapid cooling.

Extruders such as single-screw or multi-screw extruders, especially twin-screw extruders, planetary rolling extruders or ring extruders (flow tube, intensive kneader, intensive mixer or static mixer) are particularly suitable as machines for the inventive method and are preferably used. Particularly preferable are twin-screw or multi-screw extruders, especially twin-screw extruders.

It was surprising that the conversion, which in the discontinuous method needs several hours, goes to completion in a few seconds in the said machines, and in this connection that transformation of the cis to the trans form also takes place with suitable catalysis. It is a basic principle that short-time thermal treatment in interaction with the mixing effect of the intensive kneader should be sufficient to convert the reaction partners completely or very extensively. By virtue of appropriately equipped mixing chambers or appropriately assembled screw geometries, the intensive kneaders permit intensive rapid intermixing with simultaneous intensive heat exchange. In addition, steady through-flow in longitudinal direction with the most uniform dwell time possible is also assured. Moreover, different temperature regulation must be possible in the individual machine housings or sections.

The starting products are usually metered into the machines in separate product streams. In the case of more than two product streams, these may also be fed in bundled form. It is also possible to include additional catalysts and/or additives, such as leveling agents, stabilizers or adhesion promoters to this product stream. The substance streams may also be split and in this way fed to the machines in different proportions at various stations. In this way concentration gradients are selectively established, helping to achieve completeness of the reaction. The inlet station for the product streams in the sequence may be variable and manipulated so as to shift in time.

Several machines may also be combined to achieve pre-reaction and/or completion of the reaction.

The machines used for the reaction are equipped with vacuum domes, in order to remove the alcohols formed during the reaction (depending on the carboxylic acid esters used) while the reaction is still proceeding. This helps to complete the reaction by shifting the chemical equilibrium toward the desired β-hydroxyalkylamide.

Product quality may be improved by storing the product at temperatures above 40° C. for between 1 hour and four weeks, and/or by recrystallizing it.

Depending on the viscosity of the product leaving the machine or the after-reaction zone, finishing is first brought to a suitable temperature by further cooling by means of suitable equipment. This is followed by pelletization or else by size reduction to a desired particle size by means of roll-type crusher, hammer mill, cutting mill, air separation ball mill, pinned disk mill, flaking roller mill or the like.

Subject matter of the invention is also the use of the β-hydroxyalkylamides having two or three or four β-hydroxyalkylamide groups per molecule of formula I

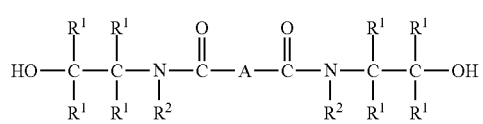

I where
$R^1$, $R^2$: independently of one another denote the same or different radicals, selected from alkyl radicals, cycloalkyl radicals, aryl radicals, aralkyl radicals or alkenyl radicals having 1-24 carbon atoms, wherein the radicals may also contain heteroatoms and/or functional groups and wherein $R^1$ may also be hydrogen and wherein $R^2$ may also be

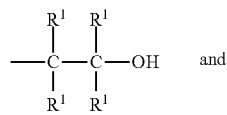

and

A:

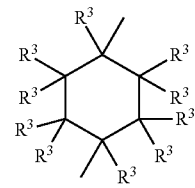

$A^1$

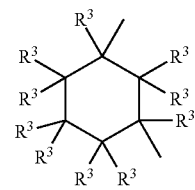

$A^2$

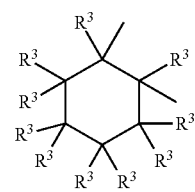

$A^3$ where $R^3$: independently of one another denote the same or different radicals, selected from hydrogen, alkyl radicals, cycloalkyl radicals, aryl radicals, aralkyl radicals or alkenyl radicals having 1-24 carbon atoms, wherein the radicals may also contain heteroatoms and/or functional groups and wherein two or more $R^3$ substituents may be linked to one another to form rings;

wherein the β-hydroxyalkylamides exist in solid form below 150° C., as cross-linking agents for carboxyl-group-containing polymers, preferably for carboxyl-group-containing polyesters.

Subject matter of the invention is also the use of the inventive β-hydroxyalkylamides in powder lacquers, preferably for carboxyl-group-containing polyester powder lacquers.

Subject matter of the invention is also the use of the inventive β-hydroxyalkylamides in powder lacquers exhibiting matte surfaces after curing (<50 gloss units, measured as reflectometer values according to DIN 67530/ISO 2813 at an angle of incidence of 60°).

Preferred subject matter of the invention is the compound N,N,N',N'-tetrakis-(2-hydroxyethyl)cyclohexyl-1,4-diamide in accordance with Formula XIIA

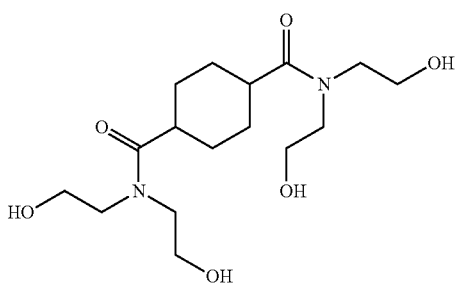

wherein this has the following parameters:

1. a trans content on the cyclohexyl ring of greater than or equal to 70 mol % relative to the total proportion of all isomers of N,N,N',N'-tetrakis-(2-hydroxyethyl)cyclohexyl-1,4-diamide that are present, and 2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C., and 3. the ratio of the enthalpies of endothermic peak 1 to endothermic peak 2 is 1:1 to 1:5, and 4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

Particularly preferred subject matter of the invention is the β-hydroxyalkylamide N,N,N',N'-tetrakis-(2-hydroxyethyl)cyclohexyl-1,4-diamide in accordance with Formula XIIA, with a trans content on the cyclohexyl ring of greater than or equal to 70 mol %, preferably greater than 80 mol % and particularly preferably greater than 85 mol % relative to the total proportion of all isomers of N,N,N',N'-tetrakis-(2-hydroxyethyl)cyclohexyl-1,4-diamide that are present.

In addition, this inventive β-hydroxyalkylamide N,N,N',N'-tetrakis-(2-hydroxyethyl)cyclohexyl-1,4-diamide in accordance with Formula XIIA has two endothermic peaks according to DSC analysis (differential scanning calorimetry): firstly is a peak with a maximum (peak 1) of approximately 160° C. and a further second peak with a maximum (peak 2) of approximately 190° C.—see the figures for the Examples. Preferably the first peak is situated in the range of 140-170° C. with a maximum of 155-165° C., and the second peak is situated in the range of 170-210° C. with a maximum of 175-207° C. Particularly preferably the first peak is situated in the range of 155-170° C. with a maximum of 158-165° C., and the second peak is situated in the range of 170-210° C. with a maximum of 180-205° C.

The ratio of the enthalpies of endothermic peak 1 (~160° C.) to endothermic peak 2 (~190° C.) can be 1:1 to 1:5, preferably 1:1 to 1:3.

The DSC measurements were carried out according to DIN EN ISO 11357-1 of March 2010. A heat-flow differential calorimeter manufactured by Mettler-Toledo, Model DSC 821, was used. The samples were heated one time from −30° C. to 250° C. at 10 K/min.

The XRPD measurements of powder samples were carried out in an x-ray diffractometer with Cu Kα radiation (1.541 Å). According to FIG. 9, the following significant and characteristic 6 peaks are found for the β-hydroxyalkylamide N,N,N',N'-tetrakis-(2-hydroxyethyl)cyclohexyl-1,4-diamide in accordance with Formula XIIA:

| Peak No. | Degrees 2 theta ± 0.2 degrees 2 theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

Most particularly preferred is the β-hydroxyalkylamide N,N,N',N'-tetrakis-(2-hydroxyethyl)cyclohexyl-1,4-diamide in accordance with Formula XIIA, with a trans content on the cyclohexyl ring of greater than or equal to 92 mol %, preferably greater than 94 mol %, particularly preferably greater than 96 mol % and most particularly preferably greater than 98 mol % relative to the total proportion of all isomers of N,N,N',N'-tetrakis-(2-hydroxyethyl)cyclohexyl-1,4-diamide that are present.

The inventive β-hydroxyalkylamide of Formula XIIA exists in solid form below 175° C., preferably below 180° C. and particularly preferably below 185° C.

The inventive β-hydroxyalkylamide of Formula XIIA with features 1. to 4. was investigated by an x-ray structure analysis of a single crystal. Detailed particulars of the measurement are summarized in Appendix 1. The x-ray structure analysis of a single crystal yielded the following result for the structure:

| | |
| --- | --- |
| Crystal system: | Orthorhombic |
| Space group: | Pbca |
| Unit cell dimensions: | a = 10.06350(10) 521   α = 90°. |
| | b = 11.85290(10) Å      β = 90°. |
| | c = 14.6275(2) Å           γ = 90°. |
| Volume: | 1744.79(3) Å$^3$ |

The numbers in parentheses indicate the measurement accuracy respectively in plus and minus for the corresponding last digit or last two digits.

Subject matter of the invention is also the compound N,N,N',N'-tetrakis-(2-hydroxyethyl)cyclohexyl-1,4-diamide in accordance with Formula XIIA

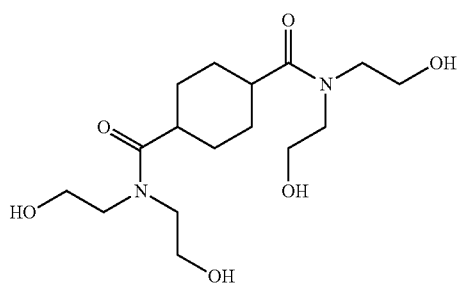

XIIA wherein this has the following parameters:
1. a trans content on the cyclohexyl ring of greater than or equal to 70 mol % relative to the total proportion of all isomers of N,N,N',N'-tetrakis-(2-hydroxyethyl)cyclohexyl-1,4-diamide that are present,
and
2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C.,
and
3. the ratio of the enthalpies of endothermic peak 1 to endothermic peak 2 is 1:1 to 1:5,
and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

5. and wherein this has, according to x-ray structure analysis of a single crystal, the following parameters:

| | | |
|---|---|---|
| Crystal system: | Orthorhombic | |
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å³ | |

Production

The particularly preferred N,N,N',N'-tetrakis-(2-hydroxyethyl)cyclohexyl-1,4-diamide in accordance with Formula XIIA can be obtained by various methods:

Firstly, as described in detail hereinabove, the N,N,N',N'-tetrakis-(2-hydroxyethyl)cyclohexyl-1,4-diamide in accordance with Formula XIIA is produced in an extruder, intensive kneader, intensive mixer or static mixer, preferably in an extruder, preferably without solvent. In this process, temperatures of 100 to 180° C. are used. This is followed by recrystallization from a suitable solvent, preferably water. After dissolution at temperatures of 20-100° C. and crystallization, the N,N,N',N'-tetrakis-(2-hydroxyethyl)cyclohexyl-1,4-diamide in accordance with Formula XIIA having the aforesaid parameters is obtained. This can then be washed with alcohols, preferably methanol, and dried. Preferably drying takes place at temperatures of 20-90° C., and it may also take place under vacuum.

A further variant of production is achieved as described in detail hereinabove, by the fact that the N,N,N',N'-tetrakis-(2-hydroxyethyl)cyclohexyl-1,4-diamide in accordance with Formula XIIA is produced in an extruder, intensive kneader, intensive mixer or static mixer, preferably in an extruder, preferably without solvent. In this process, temperatures of 100 to 180° C. are used. This is followed by heat treatment at temperatures of 50-100° C., preferably at temperatures of 70-85° C. The duration amounts to longer than 6 hours, preferably longer than 12 hours. The heat treatment may take place under vacuum.

Thus subject matter of the invention is also a method for solvent-free, continuous production of N,N,N',N'-tetrakis-(2-hydroxyethyl)cyclohexyl-1,4-diamide in accordance with Formula XIIA from dimethyl 1,4-cyclohexyldicarboxylate and diethanolamine with four β-hydroxyalkylamide groups per molecule, wherein this has the following parameters:
1, a trans content on the cyclohexyl ring of greater than or equal to 70 mol % relative to the total proportion of all isomers of N,N,N',N'-tetrakis-(2-hydroxyethyl)cyclohexyl-1,4-diamide that are present,
and
2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C.,
and
3. the ratio of the enthalpies of endothermic peak 1 to endothermic peak 2 is 1:1 to 1:5,
and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 | in an extruder, intensive kneader, intensive mixer or static mixer,
a) and recrystallization of the product obtained in this way
b) or heat treatment thereof at temperatures of 50-100° C., for a duration of longer than 6 hours.

The particularly preferred N,N,N',N'-tetrakis-(2-hydroxyethyl)cyclohexyl-1,4-diamide in accordance with Formula XIIA may also take place discontinuously in the solvent, or in other words in a batch method.

The reaction is carried out in standard reactors. This operation may take place without pressure, using a reflux condenser, or under pressure in a closed reactor.

The synthesis is carried out in a solvent, preferably in alcohols, preferably methanol. The added proportion of solvent is greater than 10 wt %, preferably greater than 15 wt % relative to the total amount of all educts (starting materials)

used. This operation may take place under reflux, or else even at relatively low temperatures as well as relatively high temperatures, under pressure.

Production takes place at temperatures of 20 to 120° C., preferably at 60 to 90° C., particularly preferably at 70 to 85° C.

After crystallization, the N,N,N',N'-tetrakis-(2-hydroxyethyl)cyclohexyl-1,4-diamide in accordance with Formula XIIA having the aforesaid parameters is obtained.

The invention also relates to a method for discontinuous production of N,N,N',N'-tetrakis-(2-hydroxyethyl)cyclohexyl-1,4-diamide in accordance with Formula XIIA from dimethyl 1,4-cyclohexyldicarboxylate and diethanolamine with four β-hydroxyalkylamide groups per molecule, wherein this has the following parameters:

1. a trans content on the cyclohexyl ring of greater than or equal to 70 mol % relative to the total proportion of all isomers of N,N,N',N'-tetrakis-(2-hydroxyethyl)cyclohexyl-1,4-diamide that are present, and
2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C., and
3. the ratio of the enthalpies of endothermic peak 1 to endothermic peak 2 is 1:1 to 1:5, and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 | in the solvent.

Moreover, the production of the N,N,N',N'-tetrakis-(2-hydroxyethyl)cyclohexyl-1,4-diamide in accordance with Formula XIIA can be carried out in closed apparatuses under pressure at temperatures of 60 to 140° C. without addition of solvent, and this is also subject matter of the invention.

The N,N,N',N'-tetrakis-(2-hydroxyethyl)cyclohexyl-1,4-diamide in accordance with Formula XIIA, produced in this way in a batch process, can be recrystallized from suitable solvents, preferably from water or alcohols, preferably from methanol.

Moreover, the production of the N,N,N',N'-tetrakis-(2-hydroxyethyl)cyclohexyl-1,4-diamide in accordance with Formula XIIA can also be achieved discontinuously without solvents. The reaction is carried out in standard reactors. This operation may take place using a reflux condenser. Preferably production takes place at temperatures of 20 to 140° C., preferably 60 to 90° C., particularly preferably 70 to 85° C. The β-hydroxyalkylamide obtained in this way in a batch process is then recrystallized from suitable solvents, preferably from water or alcohols, preferably from methanol. After crystallization, the N,N,N',N'-tetrakis-(2-hydroxyethyl)cyclohexyl-1,4-diamide in accordance with Formula XIIA having the aforesaid parameters is obtained. This method is also subject matter of the invention.

The concentration of all isomers of the N,N,N',N'-tetrakis-(2-hydroxyethyl)cyclohexyl-1,4-diamide in the end product after its production is 75 mass %, preferably 80 mass % and particularly preferably 85 mass %.

Figure 2:
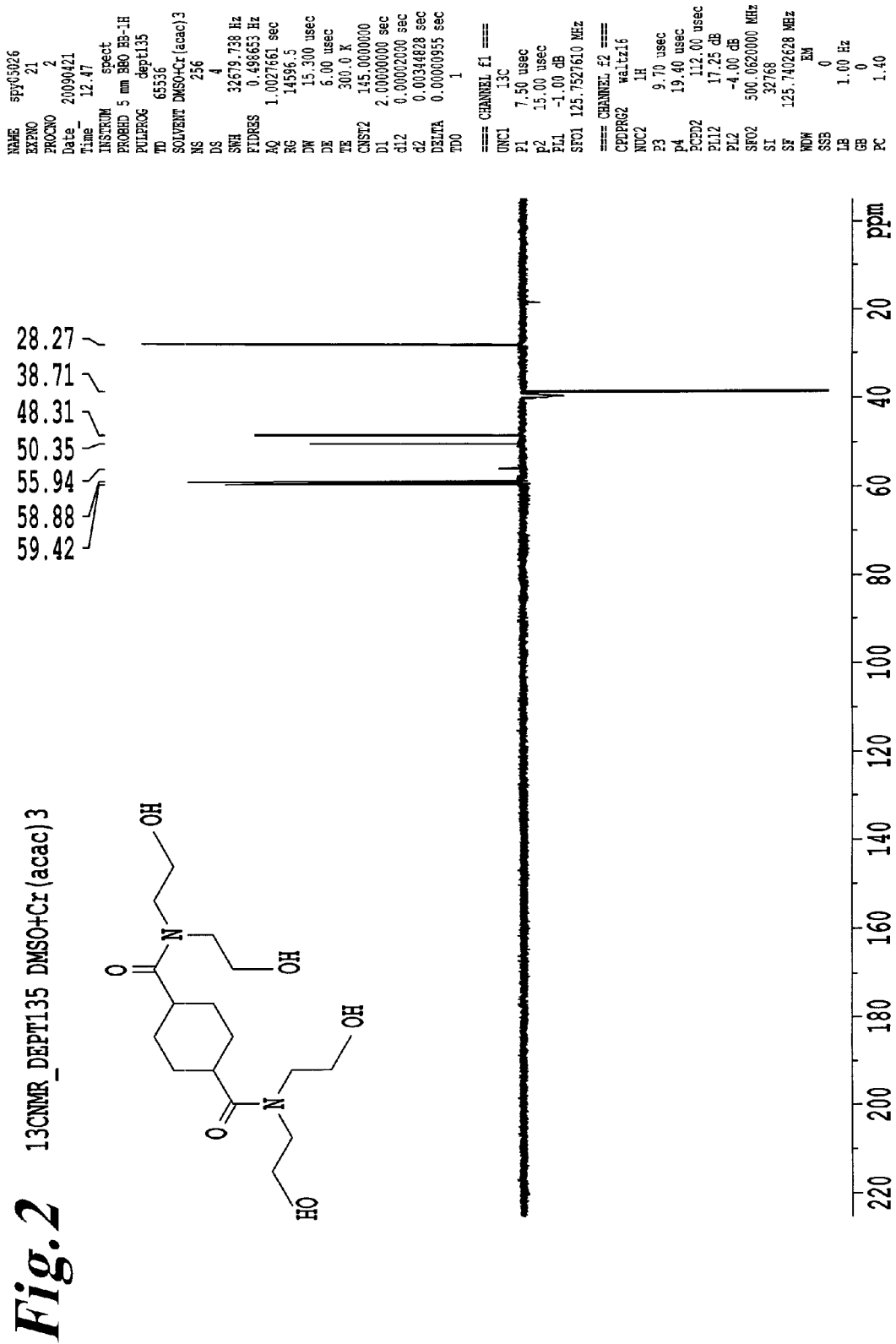
Figure 3:
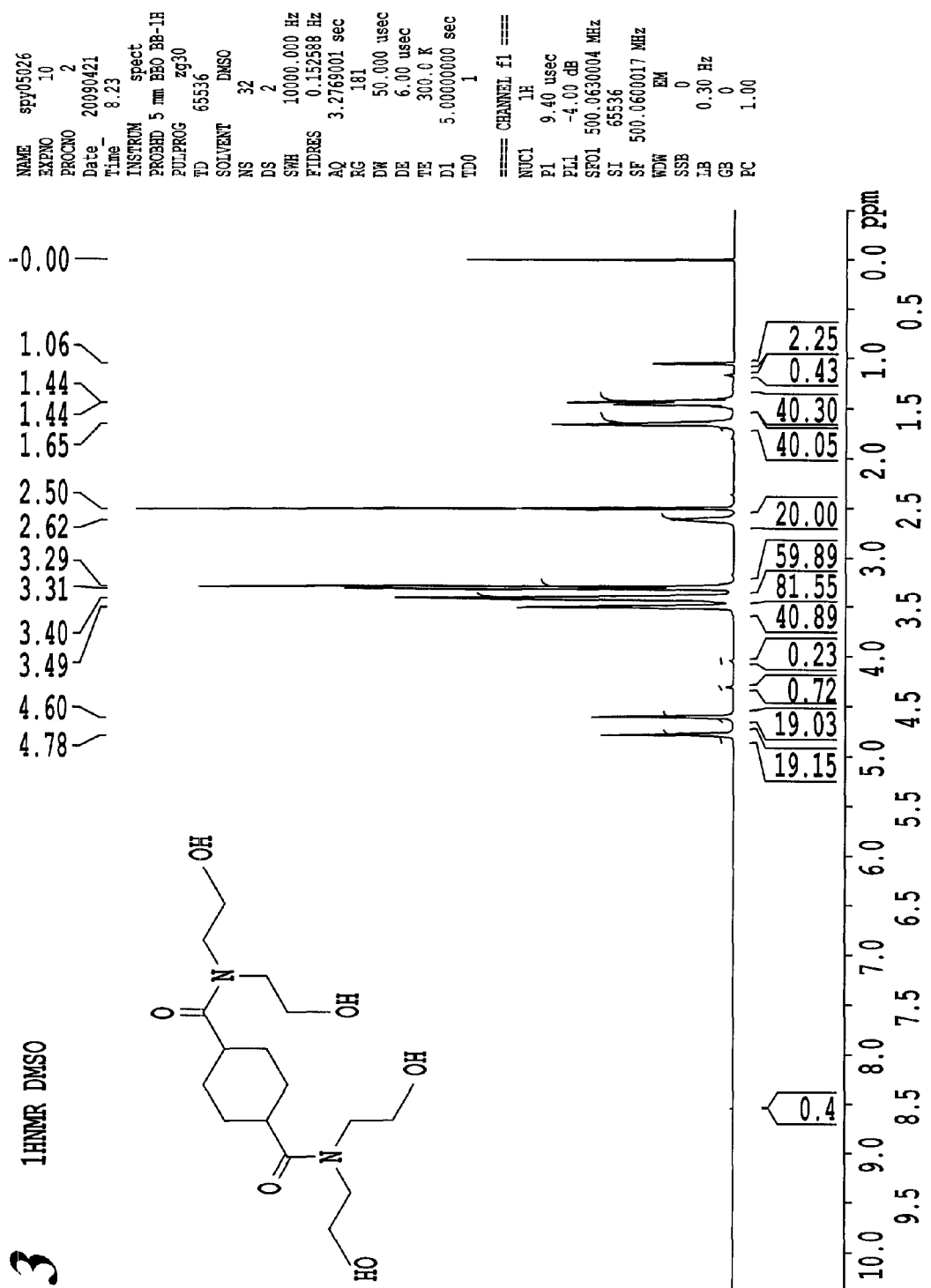
Figure 4:
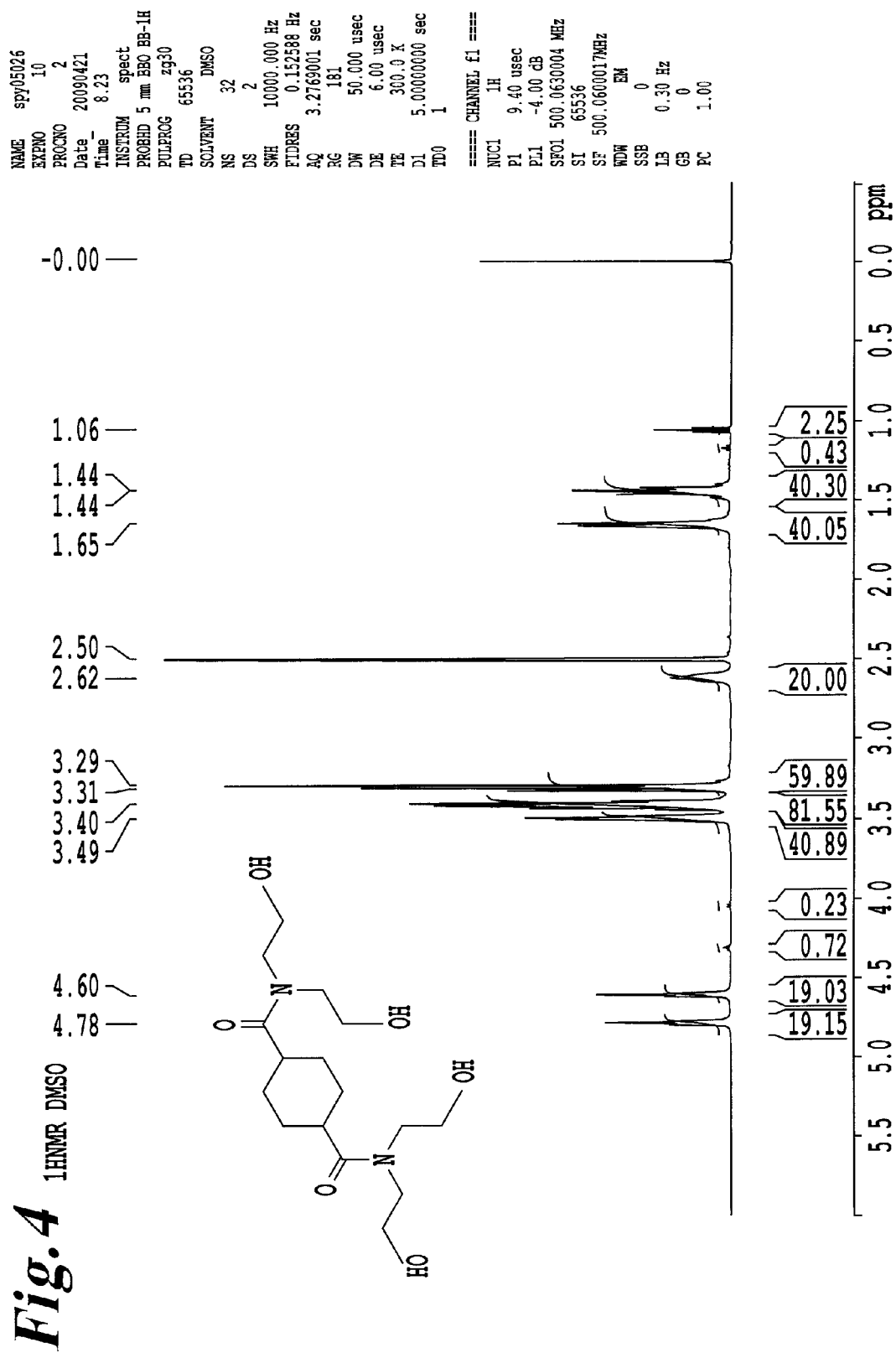

As it has been possible to show in the Examples, this β-hydroxyalkylamide N,N,N',N'-tetrakis-(2-hydroxyethyl) cyclohexyl-1,4-diamide of Formula XIIA, as described and characterized here, achieves intensive matting in powder lacquers with a gloss of less than 50 scale divisions at an angle of 60°. This product of Formula XIIA therefore differs unequivocally from the β-hydroxyalkylamide disclosed according to Korean Unexamined Application KR-2009-0111720 (and from the β-hydroxyalkylamide in Korean Ind. Eng. Chem., Vol. 20, No. 2, April 2009, 195-200), as proved therein in FIG. 2 on page 15, which exhibits only one peak at approximately 190° C. in DSC analysis and, as Comparison Example 4c shows, does not lead to coatings with matte surfaces.

Subject matter of the invention is also the use of N,N,N', N'-tetrakis-(2-hydroxyethyl)cyclohexyl-1,4-diamide in accordance with Formula XIIA

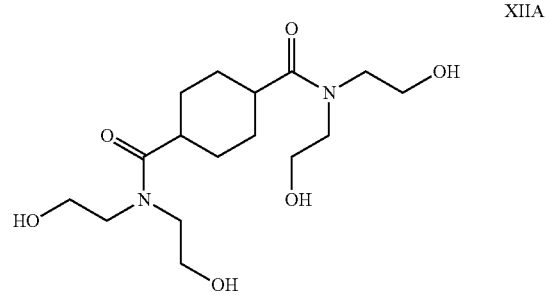 [SMILES: O=C(C1CCC(C(=O)N(CCO)CCO)CC1)N(CCO)CCO]

XIIA wherein this has the following parameters:
1. a trans content on the cyclohexyl ring of greater than or equal to 70 mol % relative to the total proportion of all isomers of N,N,N',N'-tetrakis-(2-hydroxyethyl)cyclohexyl-1,4-diamide that are present, and
2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C., and
3. the ratio of the enthalpies of endothermic peak 1 to endothermic peak 2 is 1:1 to 1:5, and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 | for the production of coatings with matte surfaces, especially in powder lacquers, preferably in carboxyl-group-containing polyester powder lacquers.

Subject matter of the invention is also the use of N,N,N',N'-tetrakis-(2-hydroxyethyl)cyclohexyl-1,4-diamide in accordance with Formula XIIA for the production of coatings having matte surfaces, with a gloss of <50 units, measured as reflectometer values according to DIN 67530/ISO 2813 at an angle of incidence of 60°.

Subject matter of the invention is also the use of N,N,N',N'-tetrakis-(2-hydroxyethyl)cyclohexyl-1,4-diamide in accordance with Formula XIIA

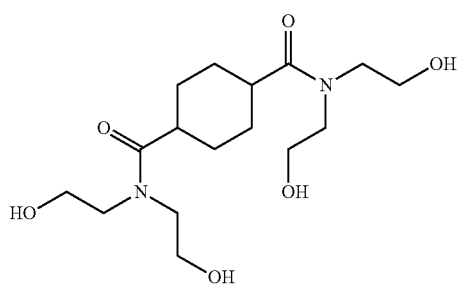

XIIA wherein this has the following parameters:
1. a trans content on the cyclohexyl ring of greater than or equal to 70 mol % relative to the total proportion of all isomers of N,N,N',N'-tetrakis-(2-hydroxyethyl)cyclohexyl-1,4-diamide that are present, and
2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C., and
3. the ratio of the enthalpies of endothermic peak 1 to endothermic peak 2 is 1:1 to 1:5, and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

5. and wherein this has, according to x-ray structure analysis of a single crystal, the following parameters:

| Crystal system: | Orthorhombic | |
|---|---|---|
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å$^3$ | |

The subject matter of the invention will be explained hereinafter on the basis of examples.

EXAMPLES

Example 1

Production of a β-Hydroxyalkylamide from Dimethyl-1,4-Cyclohexyl Dicarboxylate and Diethanolamine According to the Inventive Method

| Starting substances | Product description, manufacturer |
|---|---|
| Diethanolamine (DEA) | Dow Chemical |
| Dimethyl-1,4-cyclohexyl dicarboxylate (DMCD), trans content 15-35 mol % | Dimethyl ester of 1,4-cyclohexanedicarboxylic acid, EASTMAN |
| Sodium methylate | 30% in methanol |

Three substance streams were used:
Stream 1 comprised DMCD
Stream 2 comprised DEA
Stream 3 comprised the catalyst, in the form of methanolic sodium methylate solution.

The substance streams were metered in such a way that the molar ratio between dimethyl-1,4-cyclohexyl dicarboxylate and diethanolamine was 1:1.95.

The total amount of catalyst (sodium methylate only, calculated as solvent-free) relative to the total formulation was 0.50 to 3.0%.

Stream 1 was fed at a rate of 10.0 kg/h into the first housing of a twin-screw extruder (ZSK 30, 32 d) (temperature of the substance stream 80 to 130° C.).

Stream 2 was fed at a rate of 9.9 kg/h (temperature of the substance stream 65 to 145° C.).

Stream 3 was atomized into stream 2 (0.5 to 2.0 kg/h) upstream from the inlet into the extruder.

The extruder used comprised 8 housings, each capable of being separately heated and cooled. Housings 1-5: 160° C., housings 6-8: 120-160° C.

Housings 3, 5 and 8 were equipped with a vacuum dome (100 to 600 mbar).

The extruder screws were equipped with conveyor elements. Kneader blocks were installed upstream from the vacuum domes.

All temperatures represented target temperatures. They were regulated by electrical heating and water cooling. The extruder head was also heated electrically (100-160° C.).

The screw speed was 300 rpm. The reaction product was discharged from the extruder via a gear pump. The total throughput rate was 20 kg/h.

The end product was cooled via a length of pipe or via an extruder, passed onto a cooling belt and further cooled. The product was then recrystallized at 100° C. in demineralized water and cooled to room temperature. The mother liquor was filtered off, after which the filter cake was washed three times in methanol at room temperature and then dried in the vacuum drying oven at approximately 20 mbar and 50° C. Thereafter it was ground.

TABLE 1

End products and characterization

| Product - Example | | 1 |
|---|---|---|
| Processing | | Recrystallized |
| Trans-N,N,N',N'-tetrakis-(2-hydroxyethyl)cyclohexyl-1,4-diamide[1] | Mass % | 95.30 |
| Cis-N,N,N',N'-tetrakis-(2-hydroxyethyl)cyclohexyl-1,4-diamide[1] | Mass % | 0.28 |
| Σ N,N,N',N'-tetrakis-(2-hydroxyethyl)cyclohexyl-1,4-diamide[1] | Mass % | 95.58 |
| DEA[1] | Mass % | 0.18 |
| OH number | mg KOH/g | 616 |
| Base number | mg KOH/g | 3 |
| Melting range | °C. | 194-201 |

[1]Analytical values by GC
OH number: DIN 53240
Base number: DIN 53176
Melting range: DIN EN ISO 3146

The trans-N,N,N',N'-tetrakis-(2-hydroxyethyl)cyclohexyl-1,4-diamide (formula XII) produced was characterized by the NMR spectra in FIGS. 1-4.

Example 2

Powder Lacquer and Coating

Using the inventive β-hydroxyalkylamide (matte curing agent) from Example 1, the powder lacquer was produced in the molten state by coextrusion of all components according to Table 2 at a temperature (housing) of 90° C. (charge temperature approximately 130° C.). The composition of the raw materials is listed in Table 2. The ratio of acid groups of the polyester to OH groups of the curing agent was 1:1.

The extrudate is then cooled, ground and sieved to a grain size of <100 μm. The powder lacquer produced in this way was applied with an electrostatic powder-spraying machine at 60 kV onto degreased steel sheets (deep-drawn steel of the Krüppel Co., 210×70×0.8 mm) and/or aluminum sheets (Q-panel AL-36 5005 H 14/08 0.8 mm) and baked between 160 and 220° C. in a circulating-air drying oven. The cured lacquer films exhibited a layer thickness of approximately 55 to 65 μm. The data in the examples relate to a baking time of 20 minutes at 200° C.

Feed Substances:
1) Cross-Linking Agents:
   Inventive β-hydroxyalkylamide cross-linking agents according to Example 1.
2) Amorphous Polyesters:
   CRYLCOAT® 2617-3, acid number: 32.7 mg KOH/g, TG: 61° C. (Cytec Inc., USA)
3) Further Formulation Components:
   KRONOS® 2160 titanium dioxide (Kronos GmbH, Germany),
   RESIFLOW® PV 88 (Worlée-Chemie GmbH, Germany),
   Benzoin (Merck-Schuchard OHG, Germany)

TABLE 2

| Products | Mass % | Feed substances |
|---|---|---|
| HAA cross-linking agent | 3.00 | β-Hydroxyalkylamide Example 1 |
| Amorphous polyester | 60.70 | CRYLCOAT ® 2617-3 |
| TiO2 pigment | 35.00 | KRONOS ® 2160 |
| Leveling agent | 1.00 | RESIFLOW ® PV 88 |
| Degassing agent | 0.30 | Benzoin |
| Total | 100.00 | |

Properties of the coating:
Baking conditions: 20 minutes at 200° C.
Gloss: 33 scale divisions at 60° angle
Gloss: 42 scale divisions at 85° angle
Erichsen indentation: >8 mm
Ball impact (direct): >80 in·lb
Specular gloss: DIN 67530/ISO 2813
Erichsen indentation: DIN ISO 1520
Ball impact: DIN EN ISO 6272
DSC Measurements The DSC measurements were carried out according to DIN EN ISO 11357-1 of March 2010.

A heat-flow differential calorimeter manufactured by Mettler-Toledo, Model DSC 821, Serial No.: 5116131417 was used. The samples were heated one time from −30° C. to 250° C. at 10 K/min.

Detailed Description of the Measuring Method:
1. Type (heat-flow differential calorimeter or power-compensated calorimeter), model and manufacturer of the DSC instrument used;
2. Material, nature and type of the crucible used, and also mass if necessary;
3. Nature, purity and volume flow of the purge gas used;
4. Nature of the calibration method and details of the calibration substances used, including source, mass and further properties of importance for calibration;
5. Details of sampling, preparation of the sample element and conditioning 1: Heat-flow differential calorimeter
   Manufacturer: Mettler-Toledo
   Model: DSC 821
   Serial No.: 5116131417
2: Crucible material: ultra-pure aluminum
   Size: 40 μL, without pin
   Mettler Order No.: ME-26763
   Mass including lid: approx. 48 mg
3: Purge gas: nitrogen
   Purity: 5.0 (>99.999 vol %)
   Volume flow: 40 mL/min
4: Calibration method: single
   Material 1: indium
   Mettler Calibration Set: ME-51119991
   Mass: approx. 6 mg per weighed sample
   Calibration of temperature (onset) and heat flow
   Material 2: demineralized water
   Dispensed from the in-house system
   Mass: approx. 1 mg per weighed sample
   Calibration of the temperature (onset)
5: Sampling: from delivered sample vials
   Sample weight: 8 to 10 mg
   Sample preparation: pressed onto the crucible bottom with pestle
   Crucible lid: perforated
   Measurement program: −30 to 250° C. at 10 K/min, 1×

Description of the XRPD Measurement:

The powder sample is pressed in a powder holder and measured in the PW1800 x-ray diffractometer of Philips with Cu Kα radiation (1.541 Å) under the following conditions:
Excitation: 40 kV, 45 mA
Measurement range: 3°≤2θ≤40°
Step size: 0.1° (2 theta)

Time per step: 20 s
Rotation: ¼ revolution/sec
Receiving slit: coarse
Divergence slit: automatic

Examples 3-4

| Starting materials | Product description, manufacturer |
|---|---|
| Diethanolamine (DEA) | Dow Chemical |
| Dimethyl 1,4-cyclohexyldicarboxylate (DMCD) (distilled) trans content 15-35 mol % | Dimethyl ester of 1,4-cyclohexanedicarboxylic acid, EASTMAN |
| Sodium methylate | 30% in methanol |

Example 3a

In the three-necked flask with reflux condenser and glass stirrer there are placed 92.24 g dimethyl 1,4-cyclohexyldicarboxylate together with 96.91 g diethanolamine, 10.84 g 30% sodium methylate in methanol and 52 g methanol. A homogeneous solution is formed.

The mixture is boiled in the oil bath for six hours with stirring under reflux (bath temperature 80° C.). In the process, product begins to precipitate out after approximately 0.5 hours.

The reaction mixture is allowed to cool, whereupon further product crystallizes out. Thereafter the precipitated product is separated by filtering off the methanol and is then dried. The yield is more than 80% of theory. Table 3

Figure 5:
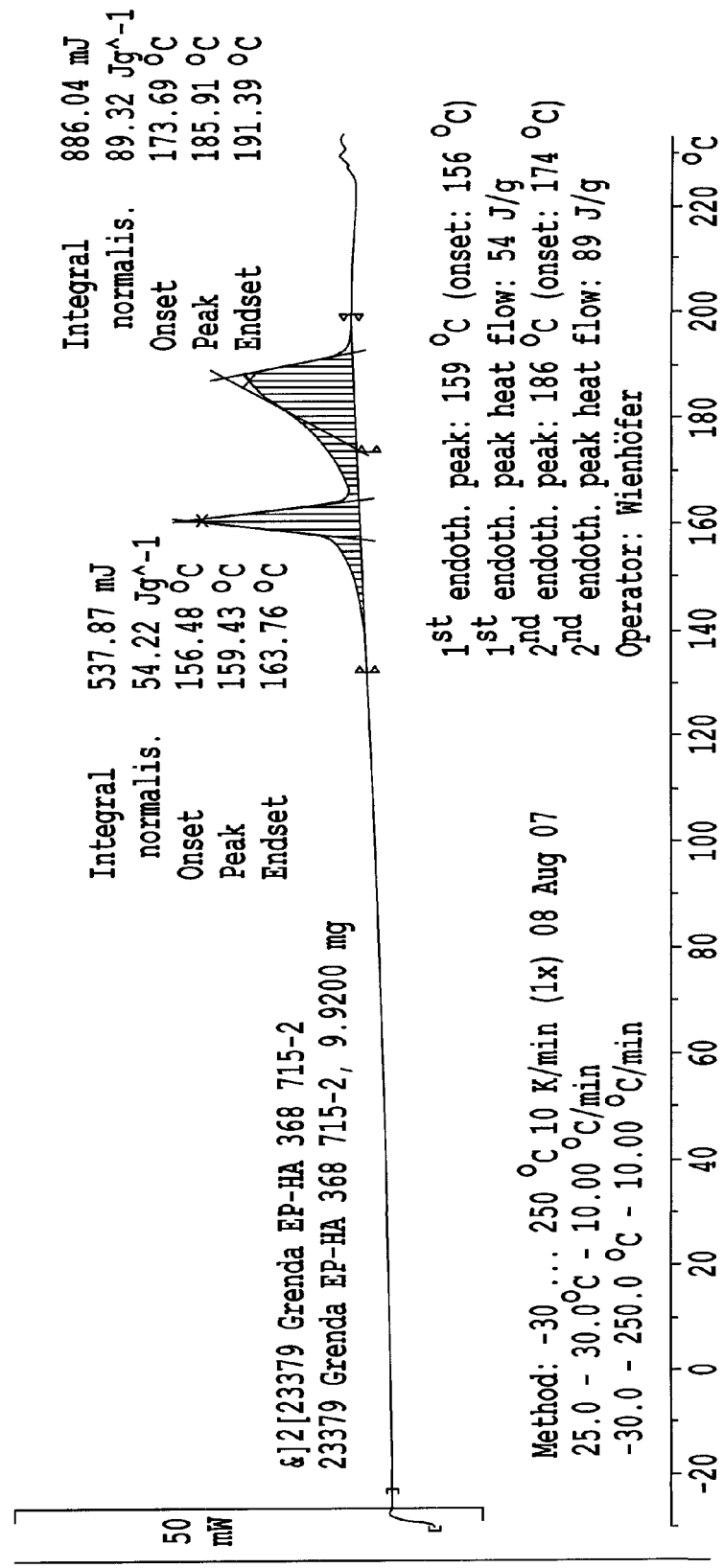
Figure 9:
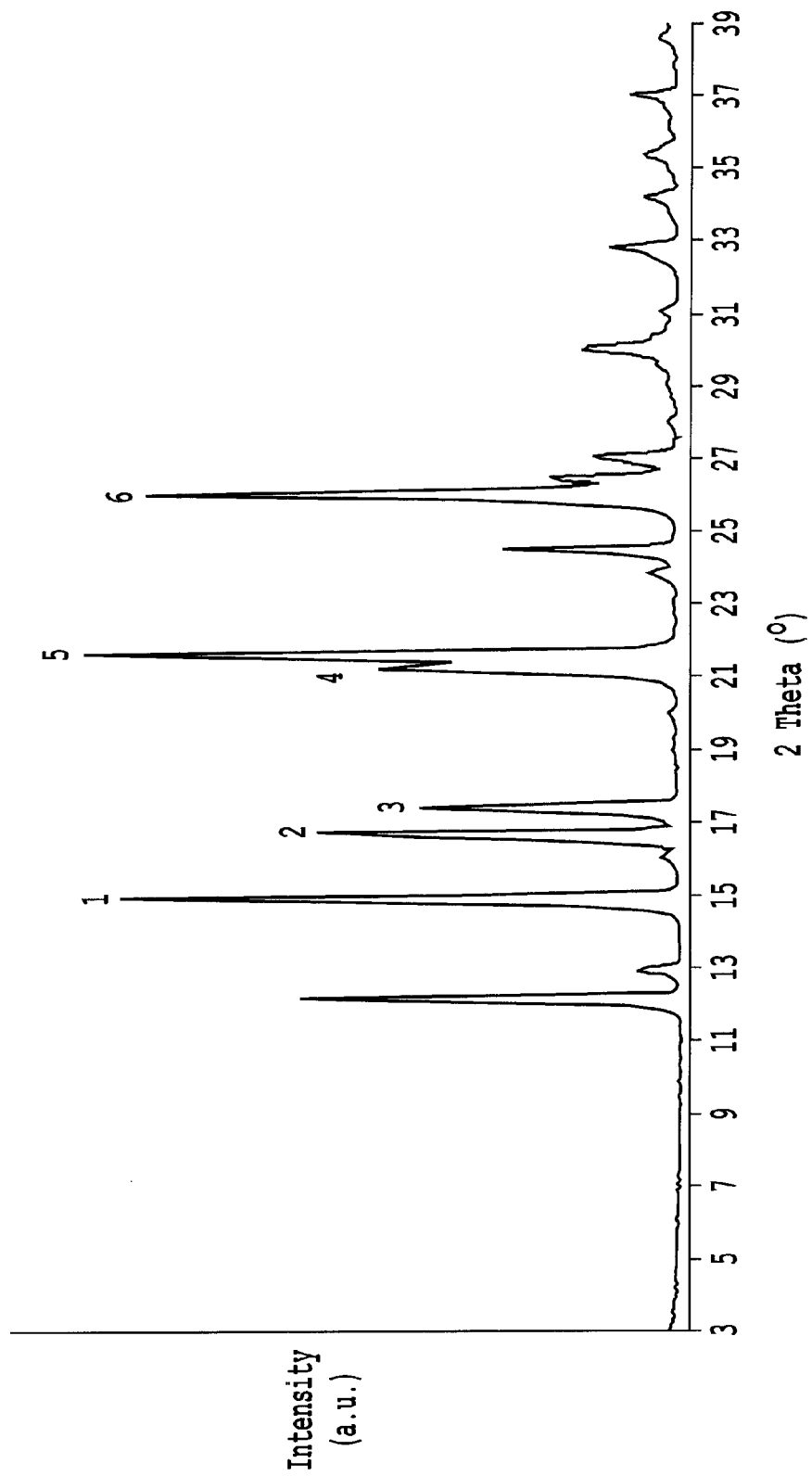

In this way there is obtained an N,N,N',N'-tetrakis-(2-hydroxyethyl)cyclohexyl-1,4-diamide in accordance with Formula XIIA with two endothermic peaks (1. at approximately 160° C. and 2. at approximately 190° C.) in the DSC according to FIG. 5 and the XRPD spectrum according to FIG. 9 and Table 5 (labeled as FIG. 12). This product produced in this way achieves intensive matting in powder lacquers having a gloss of less than 50 scale divisions at an angle of 60°, Table 3.

Example 3b

The product produced in 3a is dissolved in boiling water, slowly cooled again, then washed briefly with methanol once again after it has crystallized out. Table 3

Figure 6:
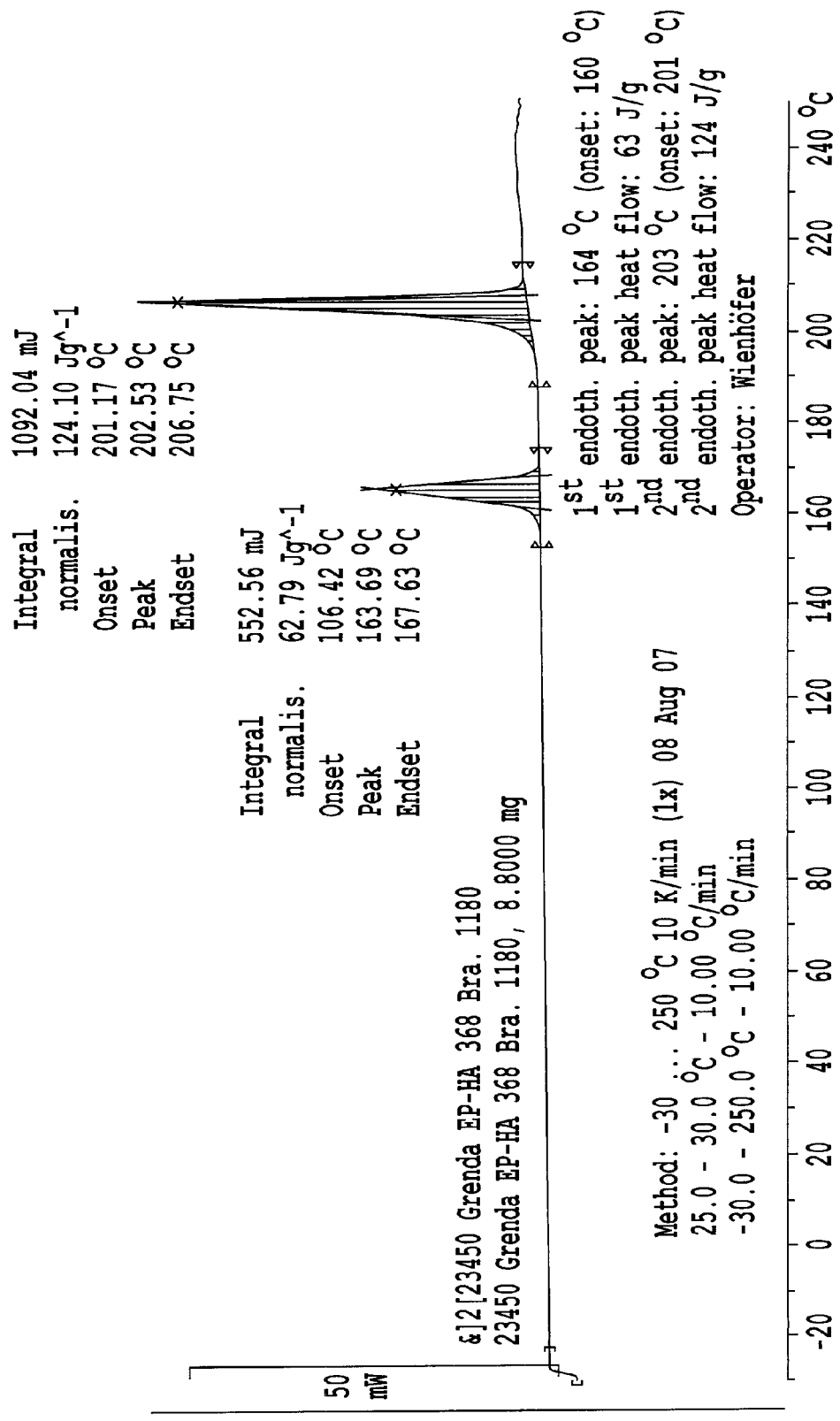
FIG. 6 shows a DSC diagram of the β-hydroxyalkylamide of Formula XIIA described in Example 3b.

This product exhibits the two endothermic peaks, see FIG. 6, while a matting effect of 29 scale divisions at an angle of 60 degrees exists in the resulting powder lacquers, Table 3.

TABLE 3

End products from discontinuous production in Examples 3a-3b and their characterization by GC analysis [1)]

| Example | | 3a | 3b |
|---|---|---|---|
| Starting material | | — | 3a |
| Processing | | Batch production as described in Example 3a | Boil 3a in demineralized water cool slowly crystallize out wash with methanol dry in vacuum |
| [1)] DEA | Mass % | 1.22 | <0.1 |
| [1)] Trans-N,N,N',N'-tetrakis-(2-hydroxyethyl)cyclohexyl-1,4-diamide | Mass % | 89.34 | 91.81 |
| [1)] Cis-N,N,N',N'-tetrakis-(2-hydroxyethyl)cyclohexyl-1,4-diamide | Mass % | 0.74 | 0.00 |
| Σ N,N,N',N'-tetrakis-(2-hydroxyethyl)cyclohexyl-1,4-diamide | Mass % | 90.08 | 91.81 |
| Ratio of [1)] trans-N,N,N',N'-tetrakis-(2-hydroxyethyl)cyclohexyl-1,4-diamide | Mol % | 99.2 | 100.0 |
| to [1)] cis-N,N,N',N'-tetrakis-(2-hydroxyethyl)cyclohexyl-1,4-diamide | Mol % | 0.8 | 0.0 |
| OH number | mg KOH/g | 629 | — |
| Base number | — | 22 | — |
| DSC: $1^{st}$ endothermic peak - Δ H | ° C. - J/g | 159 - 24 | 164 - 63 |
| DSC: $2^{nd}$ endothermic peak - Δ H | ° C. - J/g | 186 - 89 | 203 - 124 |
| Powder lacquer data | | | |
| PL experiment number | | 3a | 3b |
| HAA cross-linking agent | Mass % | 3.00 | 3.00 |
| CRYLCOAT ® 2617-3 | Mass % | 60.70 | 60.70 |
| KRONOS ® 2160 | Mass % | 35.00 | 35.00 |
| RESIFLOW ® PV 88 | Mass % | 1.00 | 1.00 |
| Benzoin | Mass % | 0.30 | 0.30 |
| Total | Mass % | 100.00 | 100.00 |
| Curing | Minutes at ° C. | 30 at 200 | 30 at 200 |
| Layer thickness | μm | 64-70 | 70-73 |
| Gloss at 60° incidence | Scale divisions | 30 | 29 |

[1)] Analytical values by GC
GC after silylation with Silyl 991 (BSTFA-TMCS 99:1) Firm of Macherey and Nagel, Order No. 701.490.150. Silylation: Heat 1 mL Silyl 991, 1 mL pyridine, 35 mg reaction product, 35 mg C-18 hydrocarbon as internal standard, 30 minutes at 80° C. in a closed ampoule.
OH number: DIN 53240
Base number: DIN 53176

Examples 4a and 4b

4a

An N,N,N',N'-tetrakis-(2-hydroxyethyl)cyclohexyl-1,4-diamide having product data 4a is produced in the extruder (Werner and Pfleiderer ZSK 30 32 d) in a manner analogous to that described in Example 1. Table 4

4b

This product described and produced as in Example 4a is recrystallized. For this purpose, the product from Example 4a is dissolved in demineralized water under boiling conditions and then slowly cooled and recrystallized, in this way transforming it once again to the solid form. Thereafter it was washed with methanol and dried at approximately 20 mbar and 50° C. in the vacuum drying oven. Table 4

Figure 7:
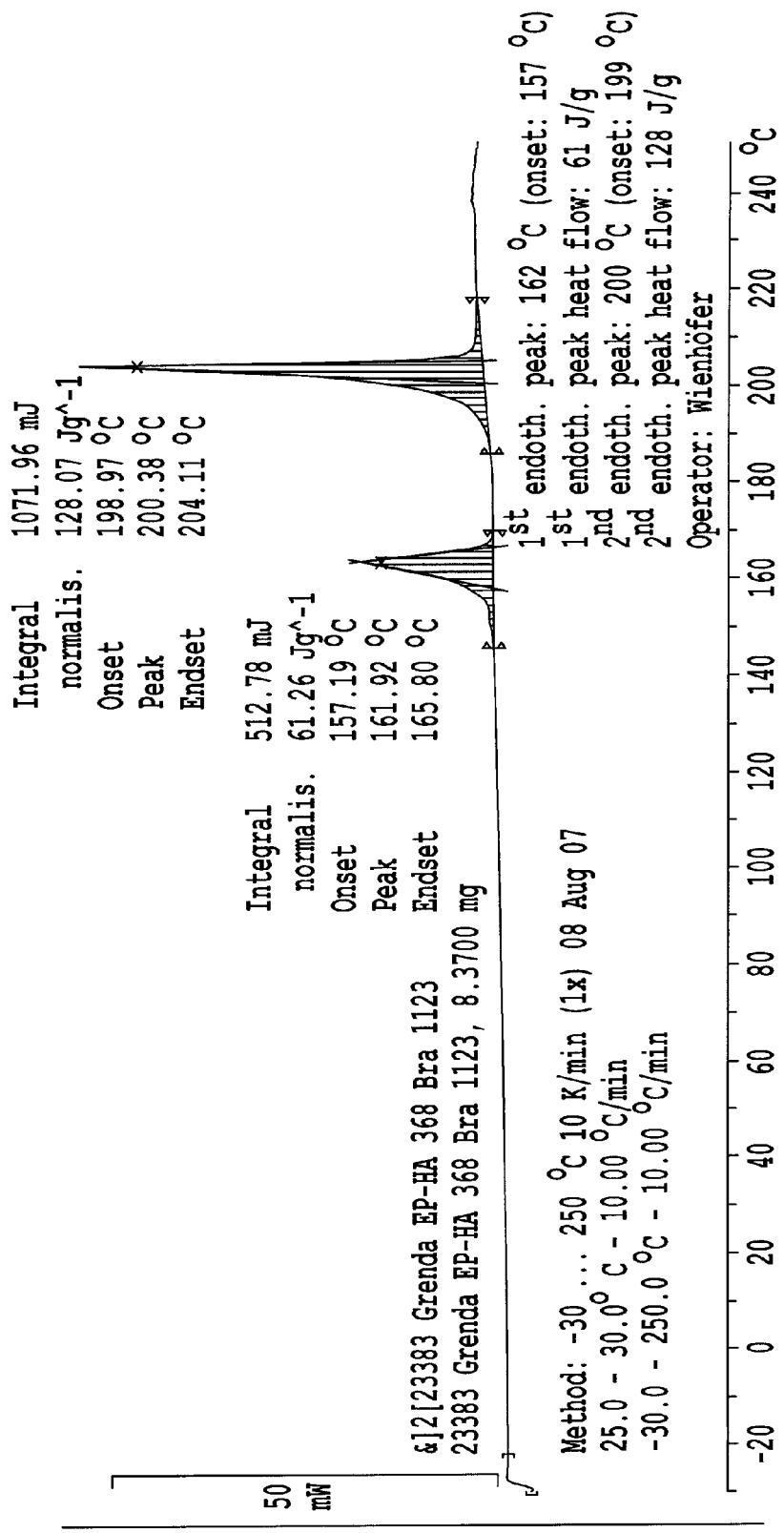
FIG. 7 shows a DSC diagram of the β-hydroxyalkylamide of Formula XIIA described in Example 4b.
Figure 11:
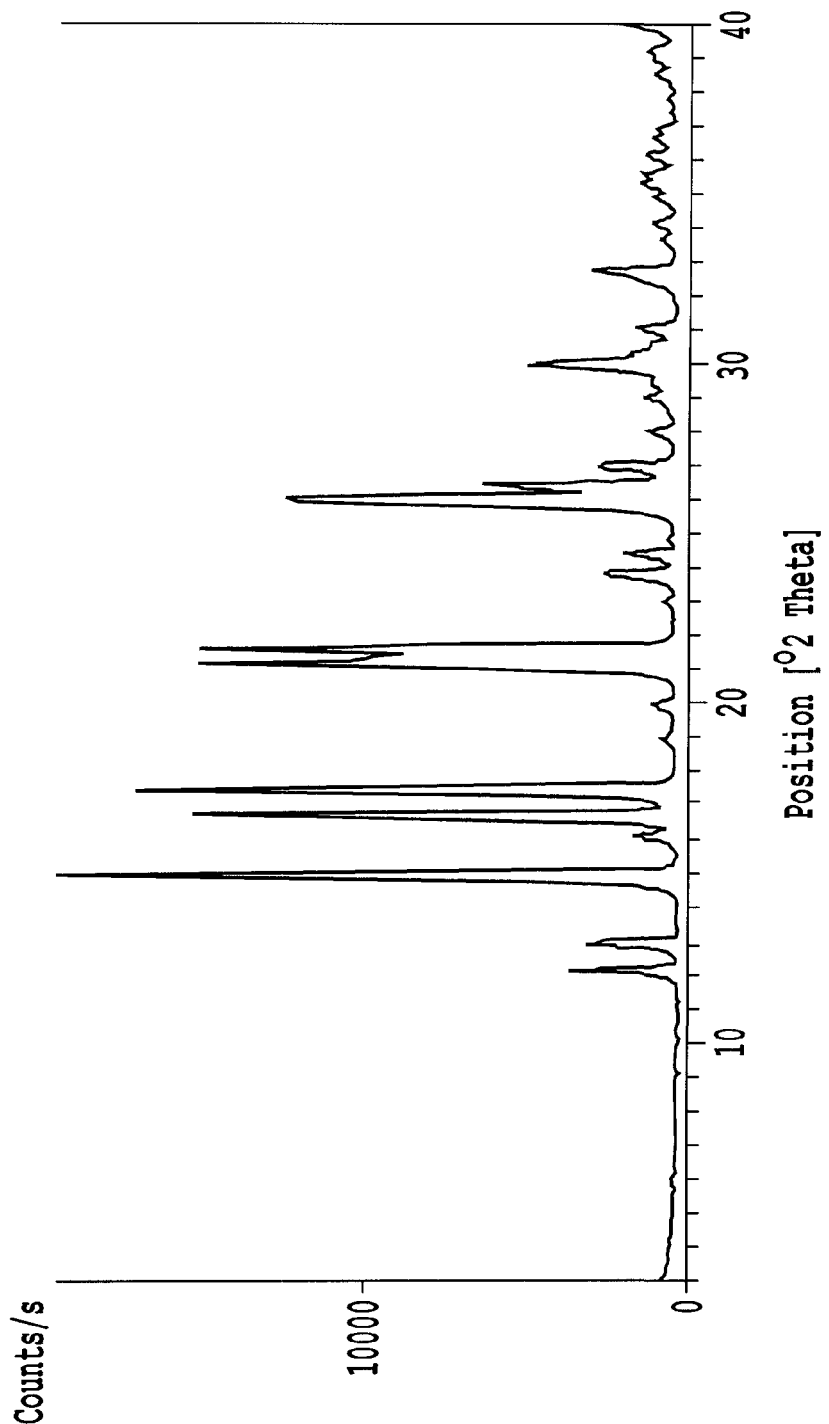
FIG. 11 shows a XRPD (x-ray powder diffraction) analysis of the β-hydroxyalkylamide of Formula XIIA (matting material) described in Example 4b.
Figure 14:
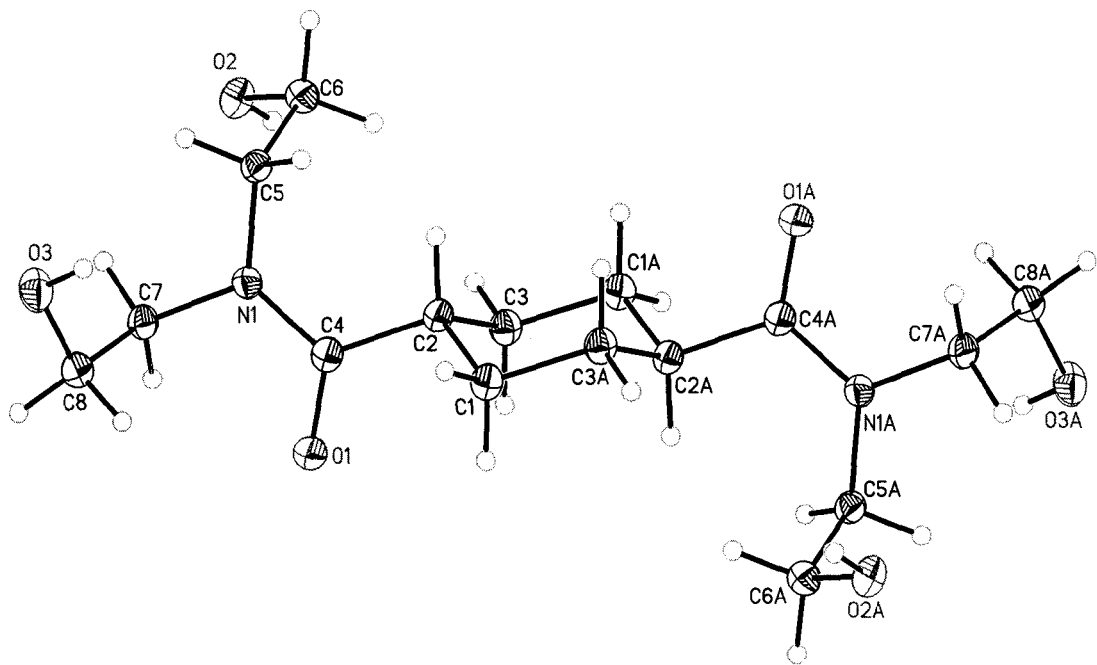
FIG. 14 shows an Ortep plot (50%) with numbering scheme.
Figure 15:
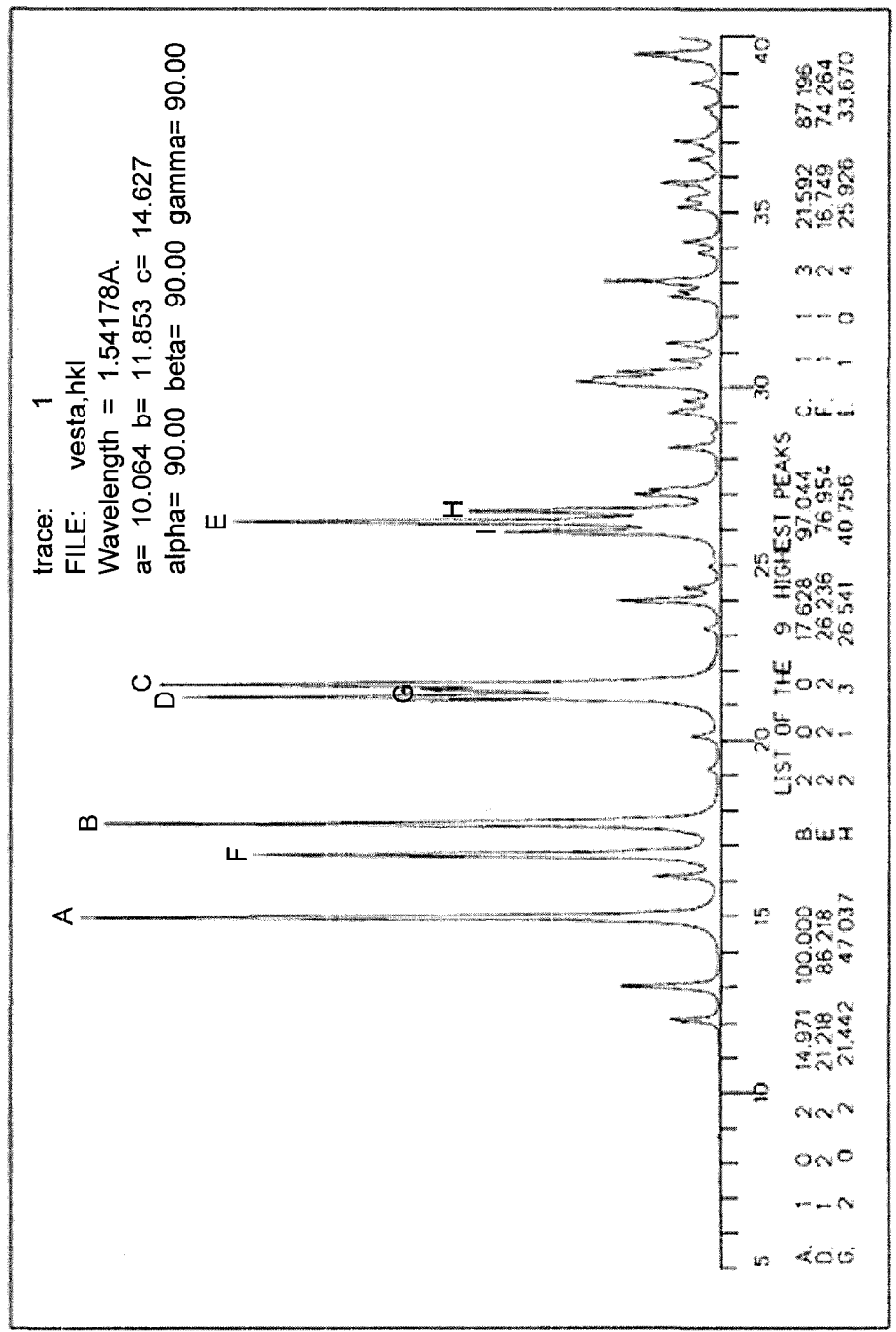
FIG. 15 shows a calculated powder diffraction diagram based on the single crystal structure determination of N,N,N', N'-tetrakis-(2-hydroxyethyl)cyclohexyl-1,4-diamide (vesta sample).

In this way there is obtained an N,N,N',N'-tetrakis-(2-hydroxyethyl)cyclohexyl-1,4-diamide with two endothermic peaks (1. at approximately 160° C. and 2. at approximately 190° C.) in the DSC. This product with the two peaks in the DSC according to FIG. 7 and the XRPD spectrum according to FIG. 11 achieves intensive matting in powder lacquers having a gloss of 30 scale divisions at an angle of 60°. Table 4

Comparison Example 4c

Figure 8:
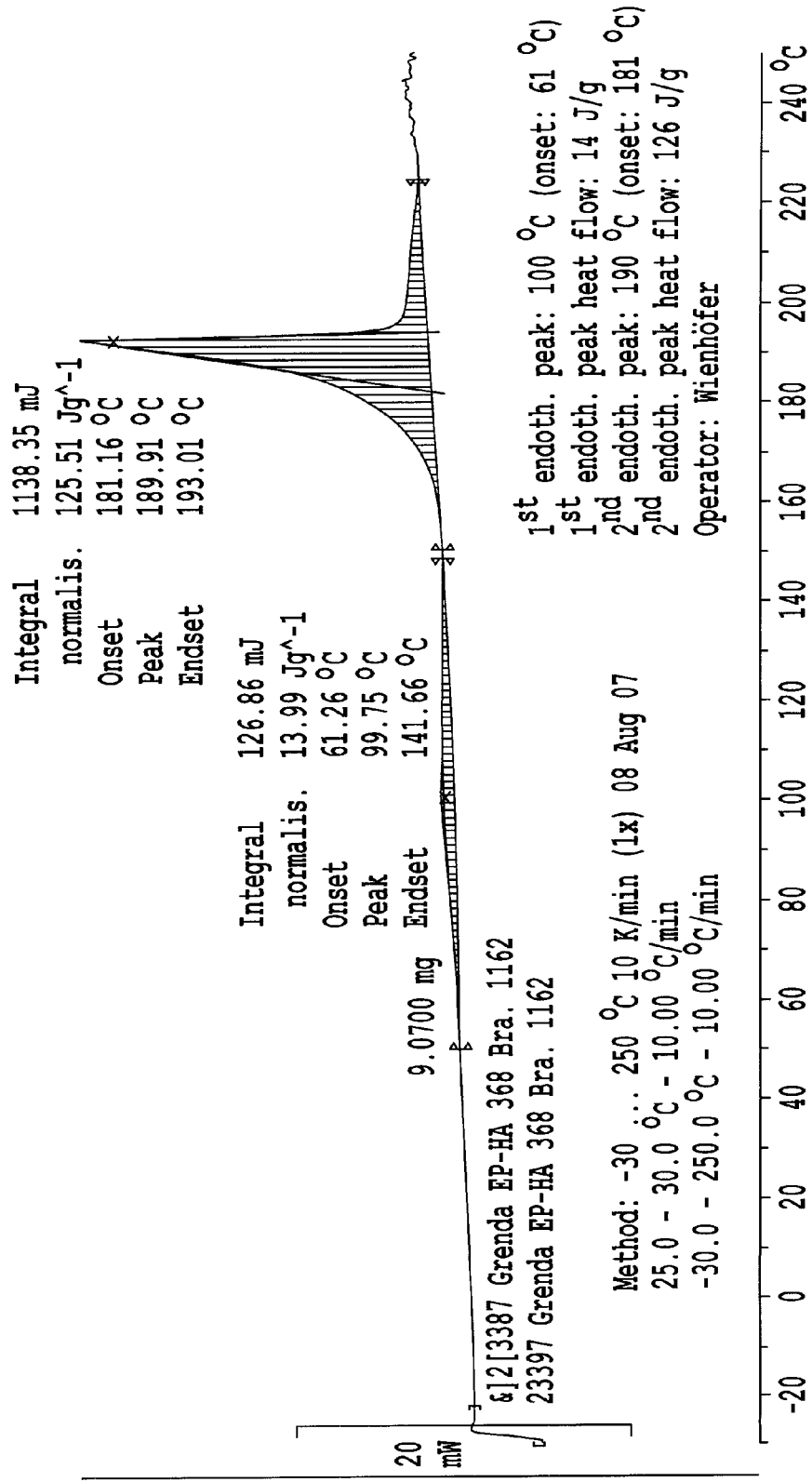
FIG. 8 shows a DSC diagram of the β-hydroxyalkylamide described in Example 4c.
Figure 10:
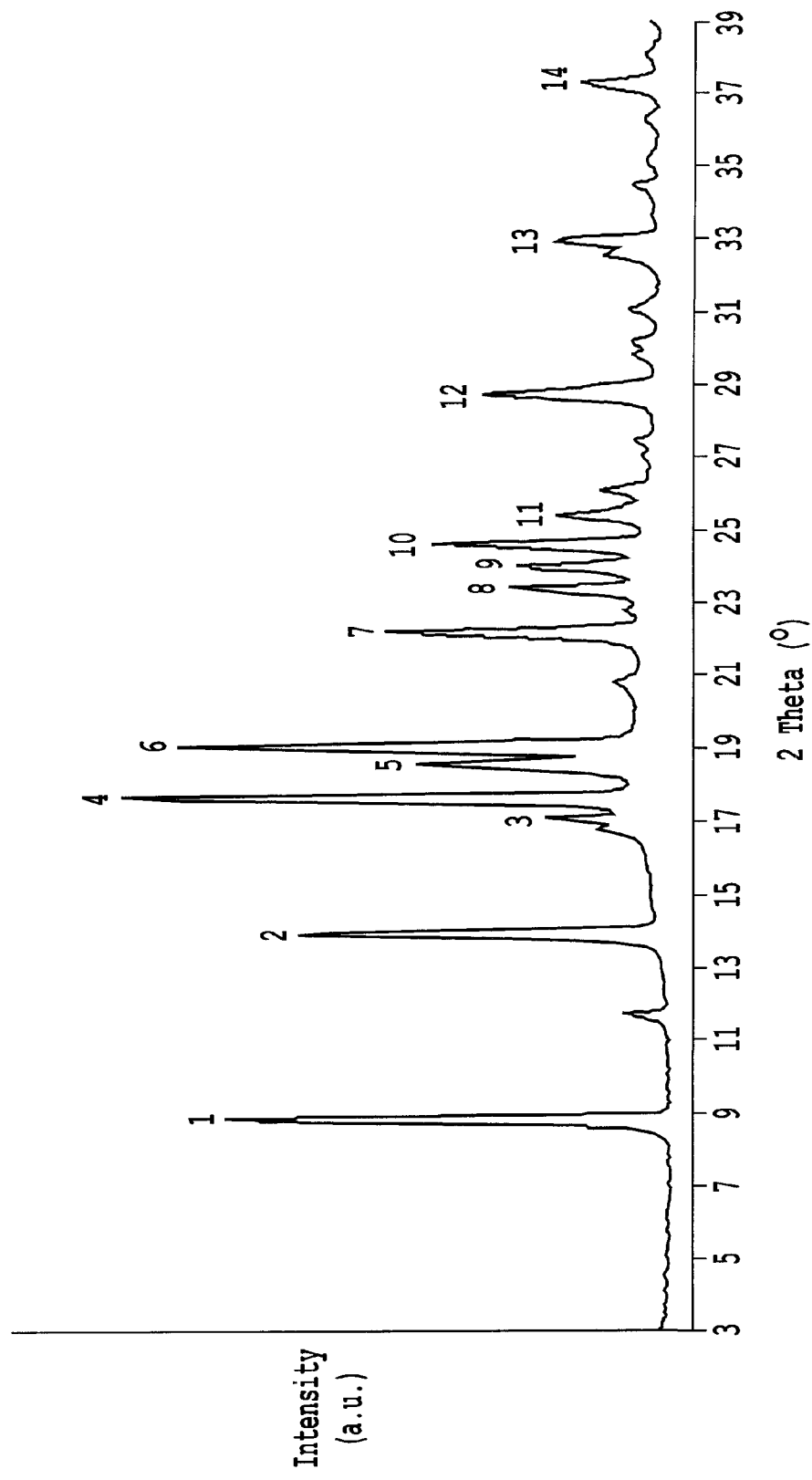
FIG. 10 shows a XRPD (x-ray powder diffraction) analysis of the β-hydroxyalkylamide (non-matting material) described in Example 4c.

A non-inventive N,N,N',N'-tetrakis-(2-hydroxyethyl)cyclohexyl-1,4-diamide having the DSC according to FIG. 8 was produced. This product exhibited only one endothermic peak at approximately 190° C. in the DSC according to FIG. 8 and an XRPD spectrum according to FIG. 10 and Table 6 (labeled as FIG. 13). The powder lacquer produced therefrom exhibits no intensive matting but instead a gloss of 95 scale divisions at an angle of 60°. Table 4

Example 4d

An N,N,N',N'-tetrakis-(2-hydroxyethyl)cyclohexyl-1,4-diamide of Formula XIIA having product data 4d is produced in the extruder (Werner and Pfleiderer ZSK 30 32 d) in a manner analogous to that described in Example 1. Table 4

This product produced in this way is conveyed on a cooling belt and collected. This material is then heat-treated in the drying oven at 80° C. for 24 hours under vacuum, and the product obtained in this way is then ground.

This product achieves intensive matting in powder lacquers having a gloss of 40 scale divisions at an angle of 60°. Table 4

TABLE 4

End products from continuous production in Examples 4a-4b and their characterization according to GC analysis [1]

| Product examples | | 4a | 4b | 4d |
|---|---|---|---|---|
| Starting material | | — | SK 988 | |
| Processing | | Extruder setting as described in Example 1 | Dissolve 4a in demineralized water cool slowly crystallize out wash with methanol dry in vacuum | Extruder setting as described in Example 1 heat treatment for 24 hours at 80° C. in vacuum |
| [1] DEA proportion | Mass % | 2.17 | 0.11 | 1.2 |
| [1] Trans-N,N,N',N'-tetrakis-(2-hydroxyethyl)cyclohexyl-1,4-diamide | Mass % | 84.25 | 93.72 | 91.3 |
| [1] Cis-N,N,N',N'-tetrakis-(2-hydroxyethyl)cyclohexyl-1,4-diamide | Mass % | 1.60 | 0.11 | 0.66 |
| Σ N,N,N',N'-tetrakis-(2-hydroxyethyl)cyclohexyl-1,4-diamide | Mass % | 85.85 | 93.83 | 91.96 |
| Ratio of [1] trans-N,N,N',N'-tetrakis-(2-hydroxyethyl)cyclohexyl-1,4-diamide | Mol % | 98.1 | 99.9 | 99.3 |
| to [1] cis-N,N,N',N'-tetrakis-(2-hydroxyethyl)cyclohexyl-1,4-diamide | Mol % | 1.9 | 0.1 | 0.7 |
| OH number | mg KOH/g | 641 | 625 | |
| Base number | — | | 24 | 1.1 |
| DSC: 1$^{st}$ endothermic peak - Δ H | ° C. - J/g | | 162 - 61 | 158 - 50 |
| DSC: 2$^{nd}$ endothermic peak - Δ H | ° C. - J/g | | 200 - 128 | 188 - 115 |

| Powder lacquer data | | | |
|---|---|---|---|
| PL experiment number | | 4b | 4d |
| HAA cross-linking agent | Mass % | 3.00 | 3.00 |
| CRYLCOAT ® 2617-3 | Mass % | 60.70 | 60.70 |
| KRONOS ® 2160 | Mass % | 35.00 | 35.00 |
| RESIFLOW ® PV 88 | Mass % | 1.00 | 1.00 |
| Benzoin | Mass % | 0.30 | 0.30 |
| Total | Mass % | 100.00 | 100.00 |
| Curing | Minutes at ° C. | 30 at 200 | 30 at 200 |
| Layer thickness | μm | 52-55 | 58-68 |
| Gloss at 60° incidence | Scale divisions | 29-30 | 40 |

TABLE 4-continued

End products from production of Comparison Examples 4c and
their characterization according to GC analysis [1] and powder lacquer

| Comparison example | | 4c |
|---|---|---|
| Starting material Processing | | allow to cool at RT |
| [1] DEA | Mass % | 2.87 |
| [1] Trans-N,N,N',N'-tetrakis-(2-hydroxyethyl)cyclohexyl-1,4-diamide | Mass % | 64.11 |
| [1] Cis-N,N,N',N'-tetrakis-(2-hydroxyethyl)cyclohexyl-1,4-diamide | Mass % | 15.84 |
| Σ N,N,N',N'-tetrakis-(2-hydroxyethyl)cyclohexyl-1,4-diamide | Mass % | 79.95 |
| Ratio of [1] trans-N,N,N',N'-tetrakis-(2-hydroxyethyl)cyclohexyl-1,4-diamide | Mol % | 80.19 |
| to [1] cis-N,N,N',N'-tetrakis-(2-hydroxyethyl)cyclohexyl-1,4-diamide | Mol % | 19.81 |
| OH number | mg KOH/g | — |
| Base number | | — |
| DSC: 1$^{st}$ endothermic peak - Δ H | ° C. - J/g | |
| DSC: 2$^{nd}$ endothermic peak - Δ H | ° C. - J/g | 171 - 87 |

| Powder lacquer data | | |
|---|---|---|
| PL experiment number | | 4c |
| HAA cross-linking agent | Mass % | 3.00 |
| CRYLCOAT ® 2617-3 | Mass % | 60.70 |
| KRONOS ® 2160 | Mass % | 35.00 |
| RESIFLOW ® PV 88 | Mass % | 1.00 |
| Benzoin | Mass % | 0.30 |
| Total | Mass % | 100.00 |
| Curing | Minutes at ° C. | 30 at 200 |
| Layer thickness | μm | 65-78 |
| Gloss at 60° incidence | Scale divisions | 95 |

[1] Analytical values by GC. GC after silylation with Silyl 991 (BSTFA-TMCS 99:1) Firm of Macherey and Nagel, Order No. 701.490.150. Silylation: Heat 1 mL Silyl 991, 1 mL pyridine, 35 mg reaction product, 35 mg C-18 hydrocarbon as internal standard, 30 minutes at 80° C. in a closed ampoule.
OH number: DIN 53240
Base number: DIN 53176

Example 5

A β-hydroxyalkylamide of Formula XIIA was produced as in Example 3a. A single crystal was grown from this. The inventive of Formula XIIA was investigated by x-ray structure analysis of a single crystal. Detailed results of the measurement are compiled in Appendix 1.

Appendix 1
Single crystal x-ray structural analysis
Analysis method: Single crystal x-ray structure analysis "2012-0573602-06D"
Report: WHC 11/11 EKS
Sample received: 2011-02-22
Report date: 2011-02-25
Objective: Determination of the single crystal structure
Compound: N,N,N',N'-tetrakis-(2-hydroxyethyl)cyclohexyl-1,4-diamide

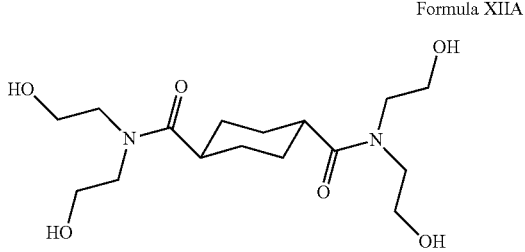 [SMILES: O=C(C1CCC(C(=O)N(CCO)CCO)CC1)N(CCO)CCO]

Formula XIIA

Crystallization: by the chemist
Crystal dimensions: colorless block, 0.50×0.40×0.40 mm$^3$
Code: vesta
Comments: The asymmetric unit contains one half molecule Experimental The single crystal structure was determined with an instrument of the firm of Oxford Diffraction, which was equipped with a CCD detector (Ruby model), a conventional x-ray tube with $Cu_{K\alpha}$ radiation, Osmic mirror as monochromator and a low-temperature system of the Cryojet type (T=100 K). Data collection was performed in phi and omega scans. Data collection and reduction were performed with Crysalis (Oxford Diffraction 2007).

Structure solution and refinement were achieved with SHELXTL (V. 6.10, Sheldrick, University of Göttingen, 2000). All non-hydrogen atoms were refined anisotropically. The hydrogen atoms were refined as riding groups.

Tables

TABLE a

Crystal data and data for structure refinement for vesta.

| Identification code | vesta |
|---|---|
| Molecular formula | C16 H30 N2 O6 |
| Formula weight | 346.42 |
| Temperature | 100 K |
| Wavelength | 1.54178 Å |

TABLE a-continued

Crystal data and data for structure refinement for vesta.

| | |
|---|---|
| Crystal system | Orthorhombic |
| Space group | Pbca |
| Unit cell | a = 10.06350(10) Å α = 90° |
| | b = 11.85290(10) Å β = 90° |
| | c = 14.6275(2) Å γ = 90° |
| Volume | 1744.79(3) Å$^3$ |
| Z | 4 |
| Density (calculated) | 1.319 mg/m$^3$ |
| Absorption coefficient | 0.832 mm$^{-1}$ |
| F(000) | 752 |
| Crystal dimensions | 0.50 × 0.40 × 0.40 mm$^3$ |
| Theta range for data collection | 6.05 to 65.68° |
| Index range | −11 ≤ h ≤ 10, −12 ≤ k ≤ 14, −14 ≤ l ≤ 17 |
| Number of reflections collected | 9191 |
| Symmetry-independent reflections | 1482 [R(int) = 0.0345] |
| Completeness to theta = 65.68° | 98.5% |
| Absorption correction | Crysalis |
| Refinement | Full matrix least squares on F$^2$ |
| Data/restraints/parameters | 1482/0/111 |
| Goodness-of-fit on F$^2$ | 1.065 |
| Final R values [I > 2 sigma(I)] | R1 = 0.0316, wR2 = 0.0792 |
| R values (all data) | R1 = 0.0358, wR2 = 0.0817 |
| Largest difference peaks | 0.199 and −0.189 e. Å$^{-3}$ |

TABLE b

Bond lengths [521] and angles[°] for vesta

| | |
|---|---|
| O(1)-C(4) | 1.2478(15) |
| O(2)-C(6) | 1.4221(15) |
| O(3)-C(8) | 1.4205(16) |
| N(1)-C(4) | 1.3479(16) |
| N(1)-C(5) | 1.4741(15) |
| N(1)-C(7) | 1.4727(15) |
| C(1)-C(3) #1 | 1.5291(17) |
| C(1)-C(2) | 1.5398(16) |
| C(2)-C(4) | 1.5189(17) |
| C(2)-C(3) | 1.5405(16) |
| C(3)-C(1) #1 | 1.5291(17) |
| C(5)-C(6) | 1.5182(16) |
| C(7)-C(8) | 1.5159(17) |
| C(4)-N(1)-C(5) | 124.59(10) |
| C(4)-N(1)-C(7) | 117.87(10) |
| C(5)-N(1)-C(7) | 117.54(9) |
| C(3) #1-C(1)-C(2) | 110.62(10) |
| C(4)-C(2)-C(1) | 110.04(10) |
| C(4)-C(2)-C(3) | 108.67(10) |
| C(1)-C(2)-C(3) | 110.09(10) |
| C(1) #1-C(3)-C(2) | 111.18(10) |
| O(1)-C(4)-N(1) | 119.97(11) |
| O(1)-C(4)-N(2) | 120.15(10) |
| N(1)-C(4)-C(2) | 119.84(10) |
| N(1)-C(5)-C(6) | 113.66(9) |
| O(2)-C(6)-C(5) | 110.97(10) |
| N(1)-C(7)-C(8) | 113.52(10) |
| O(3)-C(8)-C(7) | 113.31(10) |

Symmetry operations for generation of equivalent atoms:
1 −x + 1, −y + 1, −z

TABLE c

Torsion angles [°] for vesta

| | |
|---|---|
| C(3) #1-C(1)-C(2)-C(4) | 177.11(9) |
| C(3) #1-C(1)-C(2)-C(3) | 56.72(14) |
| C(4)-C(2)-C(3)-C(1) #1 | −178.85(9) |
| C(1)-C(2)-C(3)-C(1) #1 | −57.04(14) |
| C(5)-N(1)-C(4)-O(1) | 176.19(10) |
| C(7)-N(1)-C(4)-O(1) | −3.65(16) |
| C(5)-N(1)-C(4)-C(2) | −6.21(16) |
| C(7)-N(1)-C(4)-C(2) | 173.95(10) |

TABLE c-continued

Torsion angles [°] for vesta

| | |
|---|---|
| C(1)-C(2)-C(4)-O(1) | −54.62(14) |
| C(3)-C(2)-C(4)-O(1) | 66.61(14) |
| C(1)-C(2)-C(4)-N(1) | 127.78(11) |
| C(3)-C(2)-C(4)-N(1) | −110.98(12) |
| C(4)-N(1)-C(5)-C(6) | 80.57(13) |
| C(7)-N(1)-C(5)-C(6) | −99.58(12) |
| N(1)-C(5)-C(6)-O(2) | 61.92(13) |
| C(4)-N(1)-C(7)-C(8) | 86.25(13) |
| C(5)-N(1)-C(7)-C(8) | −93.60(12) |
| N(1)-C(7)-C(8)-O(3) | 73.97(13) |

Symmetry operations for generation of equivalent atoms:
1 −x + 1, −y + 1, −z

The invention claimed is:

1. A composition, comprising:
a reaction product of dimethyl-1,4-cyclohexyldicarboxylate and diethanolamine and having four β-hydroxyalkylamide groups per molecule according to formula (XII)

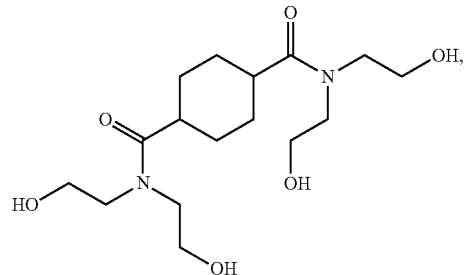

Formula (XII)

with a trans content on the cyclohexyl ring of greater than or equal to 70 mol %;

having the following parameters:

1. a trans content on the cyclohexyl ring of greater than or equal to 70 mol % relative to a total proportion of all isomers of N,N,N',N'-tetrakis-(2-hydroxyethyl)cyclohexyl-1,4-diamide that are present, and 2. two endothermic peaks according to DSC analysis (differential scanning calorimetry), peak 1 being situated in a range of 140-170° C. with a maximum of 155-165° C., and peak 2 being situated in a range of 170-210° C. with a maximum of 175-207° C., and 3. a ratio of enthalpies of endothermic peak 1 to endothermic peak 2 is 1:1 to 1:5, and 4. an XRPD spectrum of a powder sample in an x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |

-continued

| Peak No. | Degrees 2 theta ± 0.2 degrees 2 theta | d (Å) |
|---|---|---|
| 5 | 21.60 | 4.11 |
| 6 | 26.00 | 3.43, |

2. The composition of claim 1, which is in solid form in an entire temperature range below 150° C.

3. The composition of claim 1, with a trans content on the cyclohexyl ring of greater than or equal to 92 mol % relative to the total proportion of all isomers of N,N,N',N'-tetrakis-(2-hydroxyethyl)cyclohexyl-1,4-diamide that are present.

4. The composition of claim 1, which exists in solid form in an entire temperature range below 175° C.

5. An end product, comprising:
the composition of claim 1,
wherein a concentration of all isomers of the N,N,N',N'-tetrakis-(2-hydroxyethyl)cyclohexyl-1,4-diamide in said end product after production of said end product, is 75 mass %.

6. The composition of claim 1, wherein the ratio of the enthalpies of endothermic peak 1 (~160° C.) to endothermic peak 2 (~190° C.) is 1:1 to 1:3.

7. The composition of claim 1 having the following parameters:
1. the trans content on the cyclohexyl ring of greater than or equal to 70 mol % relative to the total proportion of all isomers of N,N,N',N'-tetrakis-(2-hydroxyethyl)cyclohexyl-1,4-diamide that are present, and
2. two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C., and
3. the ratio of the enthalpies of endothermic peak 1 to endothermic peak 2 is 1:1 to 1:5, and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43, |

5. and having, according to x-ray structure analysis of a single crystal, the following parameters:

| Crystal system: | Orthorhombic | |
|---|---|---|
| Space group: | Pbca | |
| Unit cell dimensions: | a = 10.06350(10) Å | α = 90° |
| | b = 11.85290(10) Å | β = 90° |
| | c = 14.6275(2) Å | γ = 90° |
| Volume: | 1744.79(3) Å³. | |

8. The composition according to claim 1, obtained by solvent-free and continuous production, comprising:
reacting starting materials in an extruder, flow tube, intensive kneader, intensive mixer, or static mixer.

9. A powder lacquer, comprising:
the composition according to claim 1; and
exhibiting matting and having an a gloss of less than 50 scale divisions at an angle of 60°.

10. A method for solvent-free and continuous production of a composition according to claim 1, comprising:
reacting starting materials in an extruder, flow tube, intensive kneader, intensive mixer, or static mixer.

11. The method of claim 10, wherein a starting material comprises at least one dialkyl-1,4-cyclohexyl dicarboxylate, having a trans content on the cyclohexyl ring of greater than or equal to 70 mol %, and existing in solid form below 150° C.

12. The method of claim 10, wherein a starting material comprises at least one dialkyl-1,4-cyclohexyl dicarboxylate of any desired trans content.

13. The method of claim 10, by intensive intermixing and short-time reaction with heat input at temperatures of >50° C., followed by isolation of an end product by cooling.

14. The method of claim 10, wherein a dwell time of feed substances ranges from 3 seconds to 15 minutes.

15. The method of claim 10, wherein reaction takes place in a single-screw, a twin-screw, or a multi-screw extruder, a ring extruder, or a planetary rolling extruder.

16. The method of claim 10 a temperature in an extruder, intensive kneader, intensive mixer, or static mixer employed, is 50 to 325° C.

17. The method of claim 10, wherein a β-hydroxyalkylamide is produced comprising dimethyl-1,4-cyclohexyldicarboxylate and diethanolamine having four β-hydroxyalkylamide groups per molecule, of formula (XII)

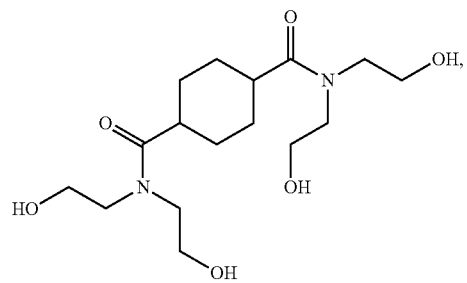

Formula (XII)

with a trans content on the cyclohexyl ring of greater than or equal to 70 mol %.

18. The method of claim 10, the method comprising reacting dimethyl 1,4-cyclohexyldicarboxylate and diethanolamine, to produce N,N,N',N'-tetrakis-(2-hydroxyethyl)cyclohexyl-1,4-diamide of formula (XIIA) with four β-hydroxyalkylamide groups per molecule

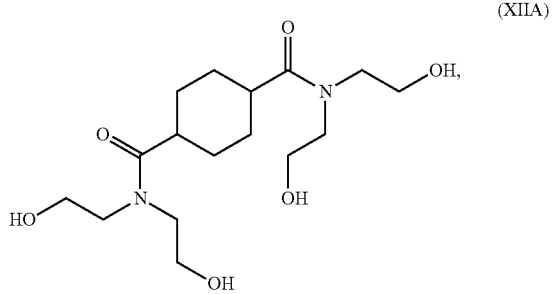 [SMILES: O=C(C1CCC(C(=O)N(CCO)CCO)CC1)N(CCO)CCO]

(XIIA)

having the following parameters:
1. a trans content on the cyclohexyl ring of greater than or equal to 70 mol % relative to a total proportion of all isomers of N,N,N',N'-tetrakis-(2-hydroxyethyl)cyclohexyl-1,4-diamide that are present, and 2. two endothermic peaks according to DSC analysis (differential scanning calorimetry), peak 1 being situated in a range of 140-170° C. with a maximum of 155-165° C., and peak 2 being situated in a range of 170-210° C. with a maximum of 175-207° C., and 3. a ratio of the enthalpies of endothermic peak 1 to endothermic peak 2 is 1:1 to 1:5, and 4. an XRPD spectrum of the powder sample in an x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43, | wherein the reacting is solvent-free, continuous, and is carried out in an extruder, intensive kneader, intensive mixer, or static mixer;

and a) recrystallizing a product obtained in this way;

or b) heat treating the product at temperatures of 50-100° C., for a duration of longer than 6 hours.

19. A method of producing a coating having a matte surface, the method comprising coating a surface with a composition according to claim 1.

20. The method of claim 19, wherein the β-hydroxyalkylamide comprises N,N,N',N'-tetrakis-(2-hydroxyethyl)cyclohexyl-1,4-diamide of formula (XIIA)

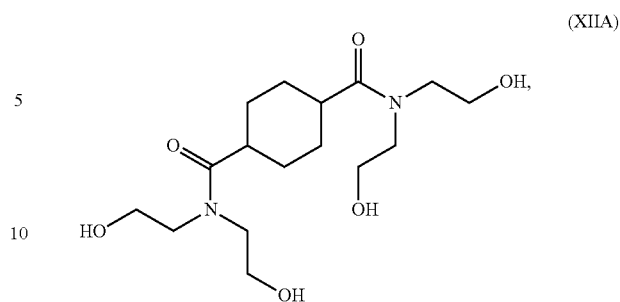

(XIIA)

having the following parameters:
1. a trans content on the cyclohexyl ring of greater than or equal to 70 mol % relative to a total proportion of all isomers of N,N,N', N'-tetrakis-(2-hydroxyethyl)cyclohexyl-1,4-diamide that are present, and 2. two endothermic peaks according to DSC analysis (differential scanning calorimetry), peak 1 being situated in a range of 140-170° C. with a maximum of 155-165° C., and peak 2 being situated in a range of 170-210° C. with a maximum of 175-207° C., and 3. a ratio of enthalpies of endothermic peak 1 to endothermic peak 2 is 1:1 to 1:5, and 4. an XRPD spectrum of a powder sample in an x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43. |

21. The method of claim 20, wherein the N,N,N',N'-tetrakis-(2-hydroxyethyl)cyclohexyl-1,4-diamide
further has the following parameters:
5. according to x-ray structure analysis of a single crystal, the following parameters:

| Crystal system: | Orthorhombic | |
|---|---|---|
| Space group: | Pbca | |
| Unit cell dimensions: | a = 10.06350(10) Å | α = 90° |
| | b = 11.85290(10) Å | β = 90° |
| | c = 14.6275(2) Å | γ = 90° |
| Volume: | 1744.79(3) Å³. | |

22. The method of claim 20, wherein the N,N,N',N'-tetrakis-(2-hydroxyethyl)cyclohexyl-1,4-diamide is comprised in a powder lacquer.

23. The method of claim 20 wherein the matte coating has <50 gloss units, measured as reflectometer values according to DIN 67530 / ISO 2813 at an angle of incidence of 60°.

24. A method of crosslinking at least one carboxyl-group-comprising polymer, the method comprising combining with the polymer, a crosslinking agent comprising the composition according to claim 1.

25. The method of claim 24, wherein the polymer is comprised in a powder lacquer.

26. A method of producing a powder lacquer, the method comprising combining the composition of claim 1 with the powder lacquer,
wherein the powder lacquer is suitable for production of a matte coating with <50 gloss units, measured as reflectometer values according to DIN 67530/ISO 2813 at an angle of incidence of 60°.

27. A method for discontinuous production of N,N,N',N'-tetrakis-(2-hydroxyethyl)cyclohexyl-1,4-diamide of formula (XIIA) with four β-hydroxyalkylamide groups per molecule, the method comprising
reacting dimethyl 1,4-cyclohexyldicarboxylate and diethanolamine, to obtain the N,N,N',N'-tetrakis-(2-hydroxyethyl)cyclohexyl-1,4-diamide of formula (XIIA)

(XIIA)

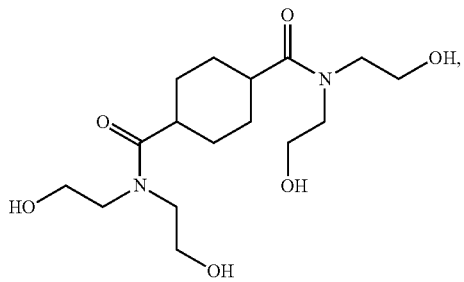

having the following parameters:
1. a trans content on the cyclohexyl ring of greater than or equal to 70 mol % relative to a total proportion of all isomers of N,N,N',N'-tetrakis-(2-hydroxyethyl)cyclohexyl-1,4-diamide that are present,
and
2. two endothermic peaks according to DSC analysis (differential scanning calorimetry), peak 1 being situated in a range of 140-170° C. with a maximum of 155-165° C., and peak 2 being situated in a range of 170-210° C. with a maximum of 175-207° C.,
and
3. a ratio of a enthalpies of endothermic peak 1 to endothermic peak 2 is 1:1 to 1:5,
and
4. an XRPD spectrum of the powder sample in an x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43, | in a solvent.

28. The method of claim 27, carried out at temperatures of 20 to 120° C.

29. The method of claim 27, wherein an added proportion of the solvent is greater than 10 wt % relative to a total amount of all starting materials employed.

30. The method of claim 27, wherein the N,N,N',N'-tetrakis-(2-hydroxyethyl)cyclohexyl-1,4-diamide has the following parameters:

1. the trans content on the cyclohexyl ring of greater than or equal to 70 mol % relative to the total proportion of all isomers of N,N,N',N'-tetrakis-(2-hydroxyethyl)cyclohexyl-1,4-diamide that are present,
and
2. the two endothermic peaks according to DSC analysis (differential scanning calorimetry), peak 1 being situated in the range of 140-170° C. with a maximum of 155-165° C., and peak 2 being situated in the range of 170-210° C. with a maximum of 175-207° C.,
and
3. the ratio of the enthalpies of endothermic peak 1 to endothermic peak 2 is 1:1 to 1:5,
and
4. the XRPD spectrum of the powder sample in the x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43, |

5. and has, according to x-ray structure analysis of a single crystal, the following parameters:

| Crystal system: | Orthorhombic | |
|---|---|---|
| Space group: | Pbca | |
| Unit cell dimensions: | a = 10.06350(10) Å | α = 90° |
| | b = 11.85290(10) Å | β = 90° |
| | c = 14.6275(2) Å | γ = 90° |
| Volume: | 1744.79(3) Å³. | |

31. A method for discontinuous production of N,N,N',N'-tetrakis-(2-hydroxyethy pcyclohexyl- 1,4-diamide of formula (XIIA) with four β-hydroxyalkylamide groups per molecule, the method comprising reacting dimethyl 1,4-cyclohexyldicarboxylate and diethanolamine, to obtain the N,N,N',N'-tetrakis-(2-hydroxyethyl)cyclohexyl-1,4-diamide of formula (XIIA)

(XIIA)

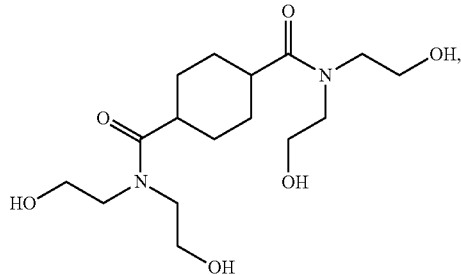

having the following parameters:
1. a trans content on the cyclohexyl ring of greater than or equal to 70 mol % relative to a total proportion of all isomers of N,N,N',N'-tetrakis-(2-hydroxyethyl)cyclohexyl-1,4-diamide that are present,
and
2. two endothermic peaks according to DSC analysis (differential scanning calorimetry), peak 1 being situated in a range of 140-170° C. with a maximum of 155-165° C., and peak 2 being situated in a range of 170-210° C. with a maximum of 175-207° C., and 3. a ratio of a enthalpies of endothermic peak 1 to endothermic peak 2 is 1:1 to 1:5, and 4. an XRPD spectrum of an powder sample in the x-ray diffractometer measured with Cu Kα radiation (1.541 Å) exhibits the following peak2s:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43, | in a closed apparatus under pressure at temperatures of 60 to 140° C. without addition of solvent.

32. A method for discontinuous production of N,N,N',N'-tetrakis-(2-hydroxyethyl)cyclohexyl-1,4-diamide of formula (XIIA) with four β-hydroxyalkylamide groups per molecule, the method comprising reacting dimethyl 1,4-cyclohexyldicarboxylate and diethanolamine, to obtain the N,N,N',N'-tetrakis-(2-hydroxyethyl)cyclohexyl-1,4-diamide of formula (XIIA)

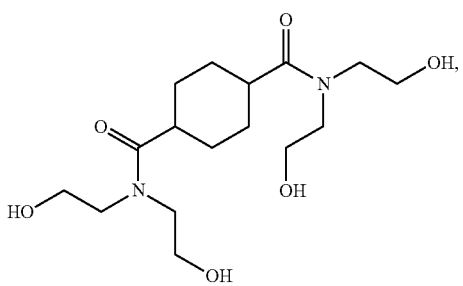

(XIIA)

having the following parameters:

1. a trans content on the cyclohexyl ring of greater than or equal to 70 mol % relative to a total proportion of all isomers of N,N,N',N'-tetrakis-(2-hydroxyethy pcyclohexyl-1,4-diamide that are present, and 2. two endothermic peaks according to DSC analysis (differential scanning calorimetry), peak 1 being situated in a range of 140-170° C. with a maximum of 155-165° C., and peak 2 being situated in a range of 170-210° C. with a maximum of 175-207° C., and 3. a ratio of a enthalpies of endothermic peak 1 to endothermic peak 2 is 1:1 to 1:5, and 4. an XRPD spectrum of the powder sample in an x-ray diffractometer measured with Cu Kα radiation (1.541 Å) exhibits the following peaks:

| Peak No. | Degrees 2 theta ± 0.2 degrees 2 theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43, | at temperatures of 20 to 120° C., without addition of solvents, and recrystallization of the product obtained in this way.

* * * * *